United States Patent
Hirotsu et al.

(10) Patent No.: US 11,150,234 B2
(45) Date of Patent: Oct. 19, 2021

(54) METHOD FOR EVALUATING TAXIC BEHAVIOR IN RESPONSE TO ODOR SUBSTANCE BASED ON OLFACTORY SENSE IN NEMATODES, AND DISH AND BEHAVIOR EVALUATION SYSTEM USED IN EVALUATION METHOD

(71) Applicant: HIROTSU BIO SCIENCE INC., Tokyo (JP)

(72) Inventors: Takaaki Hirotsu, Tokyo (JP); Takayuki Uozumi, Tokyo (JP); Satoru Kaifuchi, Tokyo (JP)

(73) Assignee: HIROTSU BIO SCIENCE INC., Tokyo (JP)

( * ) Notice: Subject to any disclaimer, the term of this patent is extended or adjusted under 35 U.S.C. 154(b) by 0 days.

(21) Appl. No.: 16/332,164

(22) PCT Filed: Sep. 11, 2017

(86) PCT No.: PCT/JP2017/032598
§ 371 (c)(1),
(2) Date: Mar. 11, 2019

(87) PCT Pub. No.: WO2018/047959
PCT Pub. Date: Mar. 15, 2018

(65) Prior Publication Data
US 2019/0369084 A1    Dec. 5, 2019

(30) Foreign Application Priority Data

Sep. 12, 2016 (JP) .............................. JP2016-177664
Mar. 31, 2017 (JP) .............................. JP2017-069762

(51) Int. Cl.
*B01L 3/00* (2006.01)
*G01N 33/493* (2006.01)

(52) U.S. Cl.
CPC ........ *G01N 33/493* (2013.01); *B01L 3/50853* (2013.01); *B01L 2300/0809* (2013.01); *B01L 2300/0848* (2013.01)

(58) Field of Classification Search
CPC ................... B01L 2300/0681; B01L 3/50855
See application file for complete search history.

(56) References Cited

U.S. PATENT DOCUMENTS

| 5,023,173 | A | 6/1991 | Horwitz et al. |
| 2014/0364386 | A1 | 12/2014 | Choe et al. |
| 2017/0016906 | A1 | 1/2017 | Hirotsu et al. |
| 2017/0107470 | A1 | 4/2017 | Fang-Yen |

FOREIGN PATENT DOCUMENTS

| EP | 3 056 085 A1 | 8/2016 | |
| JP | 2-501109 A | 4/2004 | |
| JP | 2005-47 A | 1/2005 | |
| JP | 2010-164505 A | 7/2010 | |
| JP | 2011-13070 A | 1/2011 | |
| JP | 2014-525400 A | 9/2014 | |
| WO | WO 2009/041200 A1 | 4/2009 | |
| WO | WO-2009041200 A1 * | 4/2009 | ............ G02B 21/30 |
| WO | WO 2015/029872 A1 | 3/2015 | |
| WO | WO 2015/088039 A1 | 6/2015 | |
| WO | WO 2015/200803 A1 | 12/2015 | |
| WO | WO 2016/063199 A1 | 4/2016 | |
| WO | WO 2016/147268 A1 | 9/2016 | |
| WO | WO 2017/150569 A1 | 8/2017 | |

OTHER PUBLICATIONS

English Machine Translation of WO-2009041200-A1—17 page pdf (Year: 2009).*
International Search Report dated Dec. 5, 2017 in PCT/JP2017/032598 filed on Sep. 11, 2017.
Hirotsu, T. et al., "A Highly Accurate Inclusive Cancer Screening Test Using *Caenorhabditis elegans* Scent Detection", PLoS One, Mar. 11, 2015, vol. 10, No. 3, total 15 pages.
Office Action dated Aug. 31, 2020 in corresponding Australian Patent Application No. 2017323139, 8 pages.
Goodman M. B. et al., "Thermotaxis Navigation Behavior", WormBook, ed. The C.elegans Research Community, WormBook, doi/10.1895/wormbook.1.168.1, http://www.wormbook.org/chapters/www_thermonav/thermonav.pdf [2], Feb. 20, 2014, pp. 1-10.

* cited by examiner

*Primary Examiner* — Thaian N. Ton
*Assistant Examiner* — David A Montanari
(74) *Attorney, Agent, or Firm* — Oblon, McClelland, Maier & Neustadt, L.L.P.

(57) ABSTRACT

The present invention provides a method for evaluating the taxic behavior of nematodes in response to an odor substance based on olfactory sense, and a dish and a behavior evaluation system to be used for the evaluation method.
[Solution]
Provided is a method for evaluating the taxic behavior of nematodes in response to odor of a test sample, the method including: a) providing a dish in which the test sample is arranged on the bottom surface, and nematodes are arranged in a region or a site of the bottom surface 1 cm to 3 cm away from the test sample; b) observing the arrangement of the nematodes on the bottom surface at 3 to 15 minutes after the later one of the test sample or the nematodes is arranged; and c) evaluating whether the nematodes show attraction behavior or avoidance behavior in response to the test sample, from the arrangement of the nematodes observed, and a dish or a taxic behavior evaluation system suitable for the method.

12 Claims, 13 Drawing Sheets

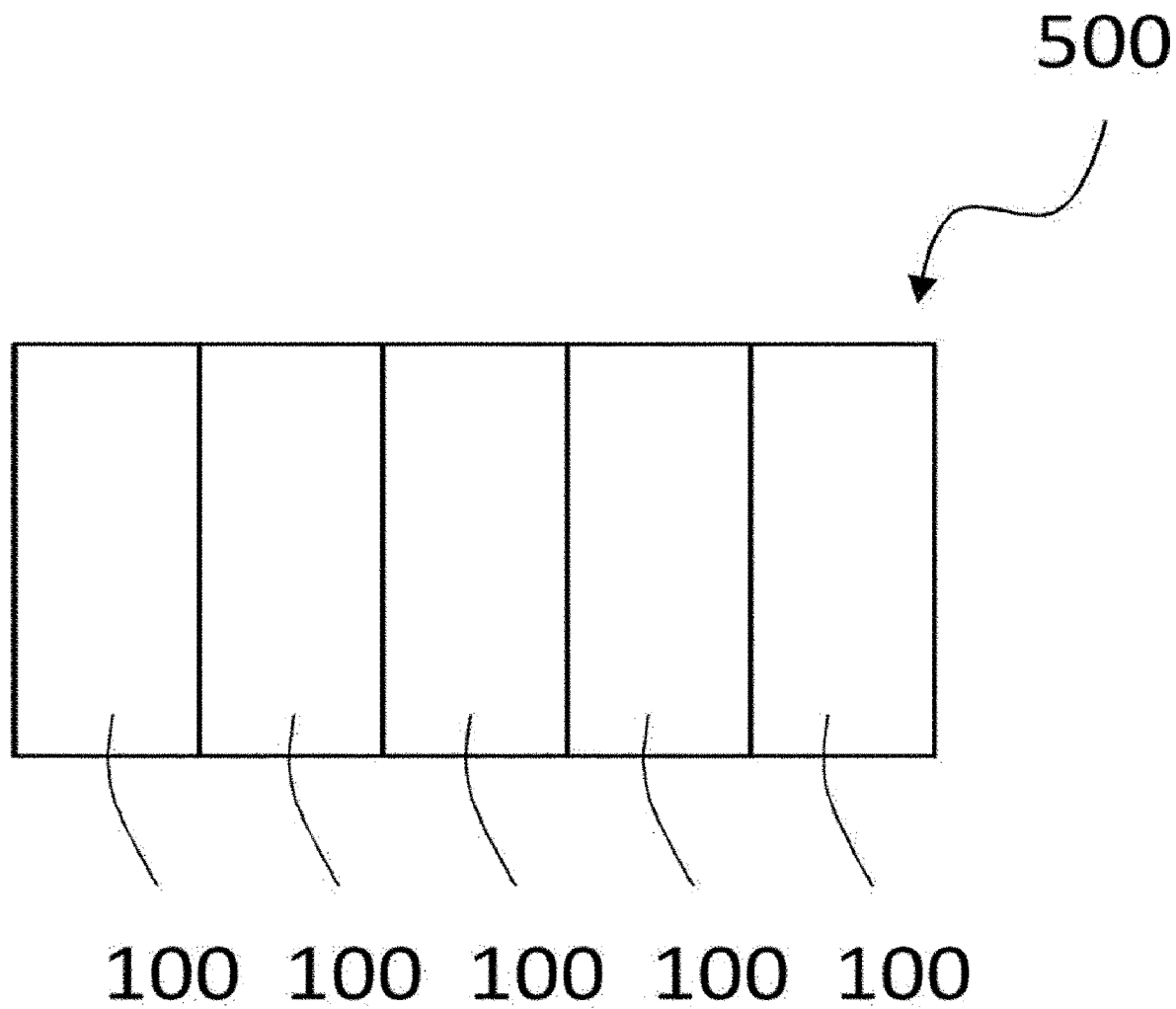

METHOD FOR EVALUATING TAXIC BEHAVIOR IN RESPONSE TO ODOR SUBSTANCE BASED ON OLFACTORY SENSE IN NEMATODES, AND DISH AND BEHAVIOR EVALUATION SYSTEM USED IN EVALUATION METHOD

CROSS-REFERENCE TO RELATED APPLICATION

This application enjoys the benefit of priority of patent applications filed in Japan on Sep. 12, 2016 (Japanese Patent Application No. 2016-177664) and on Mar. 31, 2017 (Japanese Patent Application No. 2017-69762), which are incorporated herein by reference in their entireties.

TECHNICAL FIELD

The present invention relates to a method for evaluating the taxic behavior in response to an odor substance based on olfactory sense in nematodes, and to a dish and a behavior evaluation system to be used in the evaluation method.

BACKGROUND ART

Nematodes are widely bred in the world as model organisms in biological research and are popular organisms that are the subjects of research. Nematodes have a characteristic of being easy to breed. All the nerves of nematodes have been revealed at the cellular level, and the behavior analysis has been researched actively.

In evaluating the behavior of nematodes, a 9 cm circular dish is used. This is because it is indispensable to ensure a long travel distance of nematodes, in order to maintain the accuracy in evaluating the behavior of nematodes. The present inventors have demonstrated that use of olfactory sense in nematodes enables cancer to be detected with high sensitivity and high accuracy (Non Patent Literature 1 and Patent Literature 1).

Conventionally, a test substance and nematodes are arranged on a dish so as to be isolated from each other at a certain distance or more, for evaluating the taxic behavior of nematodes through olfactory sense, and the arrangement of the nematodes on the dish has been observed as the taxic behavior, as described above. This is because, since the taxic behavior of nematodes fluctuates, and the nematodes do not necessarily move toward the test substance through the shortest distance and may exhibit a bypassing taxic behavior, it has been considered to be necessary to take an approach to evaluate only the nematodes that have moved a certain distance or more, as in general behavior evaluations, in order to improve the accuracy of the evaluation results of the taxic behavior. Further, it has been considered that, since odor can be remotely transmitted, the test can be carried out while the test sample and the nematodes are arranged at a significantly large distance from each other, and a larger distance between the test sample and the nematodes enables the taxic behavior to be evaluated more accurately. Therefore, it has been believed from above that odor is suitable for an evaluation system in which a test sample and nematodes are separated at a large distance. Accordingly, also in the evaluation of the taxic behavior through olfactory sense, use of a common behavior evaluation system has been premised.

Meanwhile, in order to allow nematodes to move a certain distance or more, it is necessary to allow the nematodes to move over a certain time or more. However, if the olfactory sense is stimulated over a certain time or more, sensitization occurs in olfactory sense in nematodes so that the nematodes start moving at random, and therefore the evaluation of the taxic behavior by olfactory sense is made impossible. Accordingly, when evaluating the taxic behavior of nematodes through olfactory sense, nematicides (powerful medicines such as sodium azide) have been used as devices to stop the movement of the nematodes that have exhibited a taxic behavior (Non Patent Literature 1 and Patent Literature 1).

CITATION LIST

Patent Literature

Patent Literature 1: WO 2015/88039

Non Patent Literature

Non Patent Literature 1: Hirotsu T. et al., PLOS ONE, 10(3): e0118699, 2015

SUMMARY OF INVENTION

The present invention provides a method for evaluating the taxic behavior in response to an odor substance based on olfactory sense in nematodes, and a dish and a behavior evaluation system for use in the evaluation method.

The present inventors have found that the taxic behavior can be evaluated with unexpectedly higher accuracy than in conventional method, by arranging a test sample and nematodes at a short distance, in the case of evaluating the taxic behavior through olfactory sense, as being different from common behavior evaluation. Further, the present inventors have invented a dish suitable for evaluating the taxic behavior of nematodes through olfactory sense based on the finding. The present invention is based on the finding and the invention.

The present invention provides the following invention.
(1) A dish having a substantially rectangular bottom surface (for example, a substantially rectangular shape of 3 to 6 cm in the longitudinal direction and 1 to 3 cm or 3 cm to 6 cm in the transverse direction), wherein the bottom surface is partitioned into at least three regions of a first region, a second region, and a third region from an end on one side toward the other end in the longitudinal direction, and the second region is arranged at the boundary between the first region and the third region.
(2) The dish according to (1) above, wherein the partition is made by forming an indented shape or printing on the upper surface or the lower surface of the bottom surface.
(3) The dish according to (1) or (2) above, further including an indicator to distinguish the first region and the third region from each other.
(4) A multiplate including a plurality of dishes according to any one of (1) to (3) above that are connected together.
(5) A method for evaluating the taxic behavior of nematodes in response to odor of a test sample, the method including:
   a) providing a dish in which the test sample is arranged, and nematodes are arranged in a region or a site on the bottom surface 1 cm to 3 cm away from the test sample;
   b) observing the arrangement of the nematodes on the bottom surface at 3 to 15 minutes after the test sample and the nematodes are arranged in the dish; and
   c) evaluating whether the nematodes show attraction behavior or avoidance behavior in response to the test sample, from the arrangement of the nematodes observed.

(6) The method according to (5) above, wherein the test sample is a sample obtained from a subject suspected to be a cancer patient.

(7) The method according to (6) above, wherein the test sample is urine obtained from a subject suspected to be a cancer patient.

(8) The method according to (6) or (7) above, further including: determining that the test sample contains an attractant derived from cancer, in the case where the nematodes show attraction behavior in response to the test sample in c); or determining that the test sample is free from attractants derived from cancer, in the case where the nematodes show avoidance behavior in response to the test sample.

(9) The method according to any one of (5) to (8) above, using no nematicides.

(10) The method according to any one of (5) to (9) above, using the dish according to any one of (1) to (3) above or any one of the dishes contained in the multiplate according to (4), in a).

The present invention also provides a solution to a new problem that the number of nematodes that penetrate into the gap between the inner wall of the dish and a solid medium increases as the size of the dish according to the aforementioned aspect decreases, and thus the number of nematodes that can be observed decreases with time.

With regard to this point, the present inventors have found that the number of nematodes that can be observed in the behavior evaluation is dramatically increased by forming a planar recess with a thickness that is equal to or larger than the thickness of the nematodes on the solid medium, completely covering the recess with a lid, and evaluating the taxic behavior based on olfactory sense within the recess, since the nematodes cannot escape from the behavior observation plane. The present invention is also based on these findings.

(1A) A taxic behavior evaluation system for evaluating the taxic behavior of nematodes including a substantially rectangular bottom surface (for example, a substantially rectangular shape of 3 to 6 cm in the longitudinal direction and 1 to 3 cm or 3 cm to 6 cm in the transverse direction) and a sidewall surrounding the periphery of the bottom surface, wherein the bottom surface is partitioned by marks into at least three regions of a first region, a second region, and a third region from an end on one side toward the other end in the longitudinal direction, and the second region is arranged at the boundary between the first region and the third region.

(2A) The taxic behavior evaluation system according to (1A) above, wherein the marks are made by forming an indented shape or printing on the upper surface or an indented shape or printing on the lower surface of the bottom surface.

(3A) The taxic behavior evaluation system according to (1A) or (2A) above, further including an indicator to distinguish the first region and the third region from each other.

(4A) A multiplate including a plurality of taxic behavior evaluation systems according to any one of (1A) to (3A) above that are connected together.

(5A) A taxic behavior evaluation system for evaluating the taxic behavior of nematodes, including: a dish in which a solid medium having a surface with a substantially rectangular planar recess (for example, 3 to 6 cm in the longitudinal direction and 1 to 3 cm or 3 cm to 6 cm in the transverse direction) having a depth that is equal to or larger than the thickness of the nematodes and 2 mm or less is introduced; and a plate that covers the recess from above.

(6A) The taxic behavior evaluation system according to (5A) above, wherein a site, corresponding to the recess, on the bottom surface of the dish is partitioned by marks into at least three regions of a first region, a second region, and a third region from an end on one side toward the other end in the longitudinal direction, and the second region is arranged at the boundary between the first region and the third region.

(7A) The taxic behavior evaluation system according to (5A) above, wherein a site, corresponding to the recess, of the plate that covers the recess from above is partitioned by marks into at least three regions of a first region, a second region, and a third region from an end on one side toward the other end in the longitudinal direction, and the second region is arranged at the boundary between the first region and the third region.

(8A) The taxic behavior evaluation system according to (6A) or (7A) above, wherein the marks are made by forming an indented shape or printing on the upper surface or an indented shape or printing on the lower surface of the bottom surface.

(9A) The taxic behavior evaluation system according to any one of (1A) to (8A) above, wherein the first region and the third region are in contact with each other, and the second region is closed.

(10A) The taxic behavior evaluation system according to any one of (1A) to (4A) above, further including a lid including a test sample seat on a surface opposed to the bottom surface when the lid is closed.

(11A) The taxic behavior evaluation system according to any one of (1A) to (10A) above, wherein the nematodes are arranged in the second region.

(12A) The taxic behavior evaluation system according to any one of (1A) to (11A) above, wherein a test sample is arranged in the first region or the third region.

(13A) A method for evaluating the taxic behavior of nematodes in response to odor of a test sample, including:
  a) providing a dish in which a test sample is arranged, and nematodes are arranged in a region or a site on the bottom surface 1 cm to 3 cm away from the test sample;
  b) observing the arrangement of the nematodes on the bottom surface at 3 to 15 minutes after the test sample and the nematodes are arranged in the dish; and
  c) evaluating whether the nematodes show attraction behavior or avoidance behavior in response to the test sample, from the arrangement of the nematodes observed.

(14A) The method according to (13A) above, wherein the test sample is a sample obtained from a subject suspected to be a cancer patient.

(15A) The method according to (14A) above, wherein the test sample is urine obtained from a subject suspected to be a cancer patient.

(16A) The method according to (14A) or (15A) above, further including: determining that the test sample contains an attractant derived from cancer, in the case where the nematodes show attraction behavior in response to the test sample in c); or determining that the test sample is free from attractants derived from cancer, in the case where the nematodes show avoidance behavior in response to the test sample.

(17A) The method according to any one of (13A) to (16A) above, using no nematicides.

(18A) The method according to any one of (13A) to (17A) above, using any one of the taxic behavior evaluation system according to any one of (1A) to (3A) above, the multiplate according to (4A), and the taxic behavior evaluation system according to any one of (5A) to (12A) above, in a).

(19A) The method according to any one of (13A) to (18A) above, using:
  (i) a dish having a substantially rectangular bottom surface (for example, substantially rectangular shape of 3 to 6 cm in the longitudinal direction and 1 to 3 cm or 3 cm to 6 cm in the transverse direction), wherein the bottom surface is partitioned into at least three regions of a first region, a second region, and a third region from an end on one side toward the other end in the longitudinal direction, and the second region is arranged at the boundary between the first region and the third region;
  (ii) a system for evaluating the taxic behavior of nematodes, including a dish in which a solid medium having a surface with a substantially rectangular planar recess (for example, 3 to 6 cm in the longitudinal direction and 1 to 3 cm or 3 cm to 6 cm in the transverse direction) having a depth that is equal to or larger than the thickness of the nematodes and 2 mm or less is introduced; and a plate that covers the recess from above; or
  (iii) any one of the dishes contained in the multiplate in which a plurality of dishes according to (i) above or taxic behavior evaluation systems according to (ii) above are connected together, in a).

According to the present invention, there are advantages that the assay time is considerably reduced, as well as the accuracy in evaluating the taxic behavior based on olfactory sense in nematodes is improved and that the need for use of deleterious materials such as sodium azide can be eliminated.

BRIEF DESCRIPTION OF DRAWINGS

FIG. 3A shows a plan view of an example 500 of a multiplate of the present invention.

DESCRIPTION OF EMBODIMENTS

In this description, "nematodes" mean *Caenorhabditis elegans*. Nematodes are widely bred in the world as model organisms in biological research and are popular organisms that are being researched, and they have a characteristic of being easy to breed and a characteristic of having excellent olfactory sense.

In this description, "cancer" means cancer species such as stomach cancer, colorectal cancer, esophagus cancer, pancreatic cancer, prostate cancer, bile duct cancer, lung cancer, blood cancer, leukemia, and lymphoma.

In this description, "subjects" mean mammals such as humans.

In this description, "taxic behavior" means attraction behavior or avoidance behavior. The attraction behavior means a behavior of decreasing a physical distance from a substance, and the avoidance behavior means a behavior of increasing a physical distance from a substance. Substances that induce the attraction behavior are called attractants, and substances that induce the avoidance behavior are called repellents.

Nematodes (*C. elegans*) have properties of being attracted to attractants and avoiding repellents by olfactory sense. The behavior of being attracted to attractants is referred to as attraction behavior, and the behavior of avoiding repellents is referred to as avoidance behavior. Further, attraction behavior and avoidance behavior are collectively referred to also as taxic behavior.

The present invention provides a behavior evaluation system (for example, a dish shown in the following embodiments and a lid thereof, as required) that is suitable for evaluating the taxic behavior of nematodes through olfactory sense. The dish and the lid can be made of resin such as plastic and can be made of transparent resin. Hereinafter, the present invention will be described for each embodiment. Hereinafter, the expression, partition line, is used in the meaning of a line partitioning between regions as a mark, not physically separating the regions. In the behavior evaluation, nematodes can move into another region over the partition line.

First Embodiment

The first embodiment of the present invention will be described with reference to FIGS. 1A and 1B.

Figure 1A:
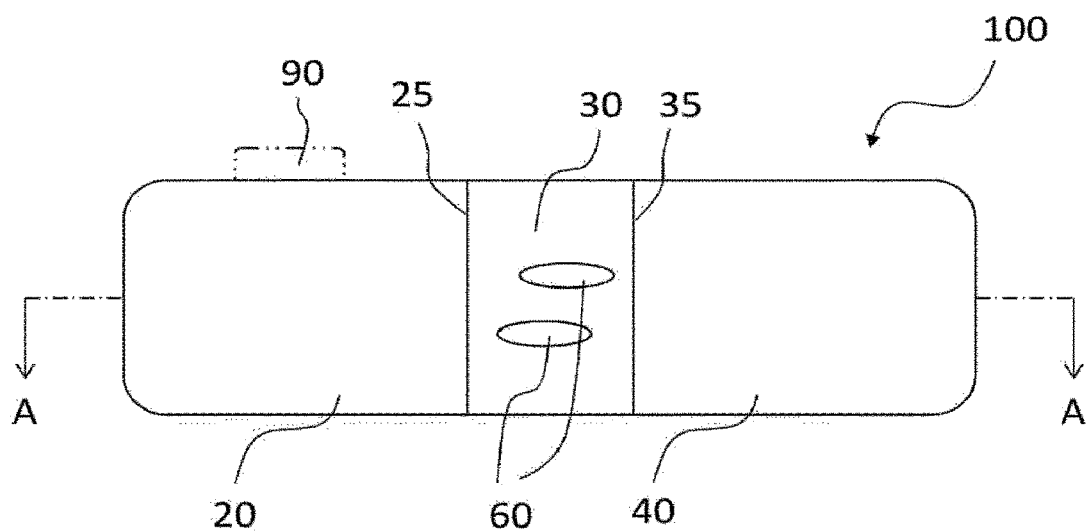
FIG. 1A shows a plan view of a dish 100 of the first embodiment of the present invention. In the figure, the dashed-double-dotted line indicates the boundary line of the partition pattern on the bottom surface.

As shown in FIG. 1A, the dish 100 in this embodiment is a dish having a substantially rectangular bottom surface. The bottom surface of the dish 100 has at least two partition lines 25 and 35 partitioning the bottom surface area into at least three regions from an end on one side toward the other end in the longitudinal direction. Thereby, the bottom surface is partitioned into at least three regions of a first region 20, a second region 30, and a third region 40, particularly, the second region 30 is arranged at the boundary between the first region 20 and the third region 40. The dish 100 has a sidewall extending upwardly so as to surround the periphery of the bottom surface. Further, as shown in FIG. 1I, an inner bottom surface 100a of the dish 100 is substantially perpendicular to the sidewall. Further, the inner bottom surface 100a of the dish 100 is substantially parallel to an outer bottom surface 100b.

The dish 100 of the first embodiment can be a dish having a substantially rectangular bottom surface, where the length of the bottom surface in the longitudinal direction can be 3 cm to 6 cm, and the length thereof in the transverse direction can be in the range of 1 cm to 3 cm or 3 cm to 6 cm. The length in the longitudinal direction can be preferably 4 cm to 6 cm, preferably 4.5 cm to 5.5 cm, preferably 5 cm. The length in the transverse direction can be preferably 1.5 cm to 2.5 cm, preferably 2 cm. Alternatively, the length in the transverse direction can be preferably 3.5 cm to 5.5 cm, preferably 4 cm to 5 cm. Further, the dish 100 of the first embodiment can have a substantially rectangular bottom surface, where the length of the bottom surface in the longitudinal direction can be 4 cm to 6 cm, preferably 4.5 cm to 5.5 cm, and the length of the bottom surface in the transverse direction can be 1.5 cm to 2.5 cm or 3.5 cm to 5.5 cm. The dish 100 of the first embodiment may have a substantially rectangular bottom surface, where the length in the longitudinal direction may be 4.5 cm to 5.5 cm, and the length in the transverse direction may be 4.5 cm to 5.5 cm. Further, the dish 100 of the first embodiment can have a height of 1 cm to 3 cm.

The second region 30 may be arranged so as to separate the first region 20 and the third region 40 from each other. As shown in FIG. 1A, the second region 30 can be preferably arranged so that the first region 20 and the third region 40 are opposed to each other with the second region 30 interposed therebetween.

The second region 30 can be 30% or less, 25% or less, 20% or less, 15% or less, 10% or less, or 5% or less, in the total area of the bottom surface.

Any partition may be employed, as long as humans or machines can distinguish the at least three regions from one another. In particular, the partition needs only to be such that the boundaries between the regions can be visually perceptible and does not completely prevent the movement of nematodes between the regions. The partition can be made so that nematodes can move between the regions. The partition is not specifically limited but can be made, for example, by printing on the bottom surface or forming an indented shape on the bottom surface. The printing on the bottom surface or forming the indented shape on the bottom surface may be applied to either the upper surface or the lower surface of the bottom surface. As shown in FIG. 1A, the partition can be made by partition lines that serve as boundary lines such as the partition line 25 and the partition line 35. The partition lines are not necessarily straight lines but can be preferably straight lines. The partition lines do not necessarily form the indented shape.

The first region 20 and the third region 40 may have indicators so that the first region and the third region can be distinguished from each other. The indicators may be symbols such as balloon mark and x-mark, or may be characters or some marks. In order to distinguish the first region and the third region from each other, the dish 100 may have a tag 90. The first region and the third region may have different areas so that they can be distinguished using the difference in area.

The tag 90 can be used, for example, for distinguishing a plurality of dishes 100 from each other. An indicator such as a barcode and a two-dimensional barcode can be attached to the tag 90, and the indicator can include the management information of each dish 100, though there is no specific limitation thereto.

Figure 1B:
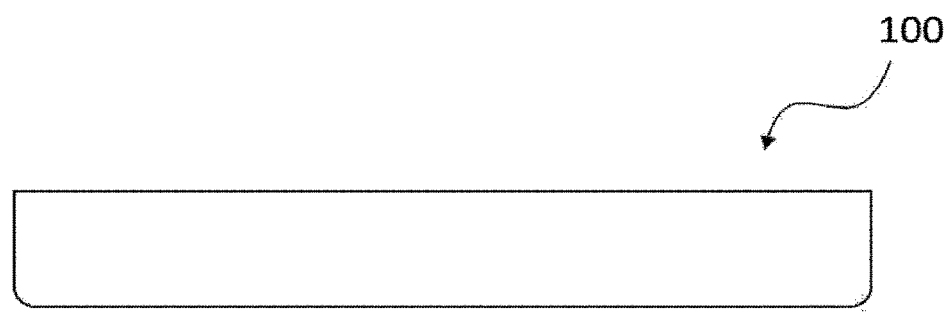
FIG. 1B shows a front view of the dish 100 of the first embodiment of the present invention.

The dish 100 has a sidewall along the edge of the bottom surface to have a container shape, as shown in FIG. 1B.

Usage of Dish of First Embodiment

The dish 100 of the first embodiment is suitable for evaluating the taxic behavior of nematodes through olfactory sense. Hereinafter, a method for evaluating the taxic behavior of nematodes through olfactory sense using the dish 100 of the first embodiment will be described.

A solid medium for nematodes can be added into the dish 100 of the first embodiment. The solid medium is, for example, an agar medium, and those skilled in the art would be able to produce a culture medium suitable for the survival of nematodes and add it to the dish.

Nematodes 60 can be disseminated into the second region 30. The nematodes may be disseminated onto the entire surface of the second region 30 or may be disseminated into only a part of the second region 30. A test sample can be arranged in the first region 20 or the third region 40, for example, at a position about 1 cm to 3 cm away from the region into which nematodes are disseminated.

When nematodes are disseminated into the dish 100 of the first embodiment in which the test sample has been arranged, the nematodes show attraction behavior toward the test sample so as to move to a place close to the test sample in the case where the test sample is an attractant, whereas the nematodes show avoidance behavior from the test sample so as to move to a place away from the test sample in the case where the test sample is a repellent. Accordingly, whether the test sample is an attractant or a repellent can be determined by observing the place to which the nematodes have moved (from the arrangement of the nematodes observed). The observation can be carried out, for example, by visual inspection or using a microscope. The observation may be performed by imaging the arrangement information of the nematodes and using the image.

Modified Example of First Embodiment

Figure 1C:
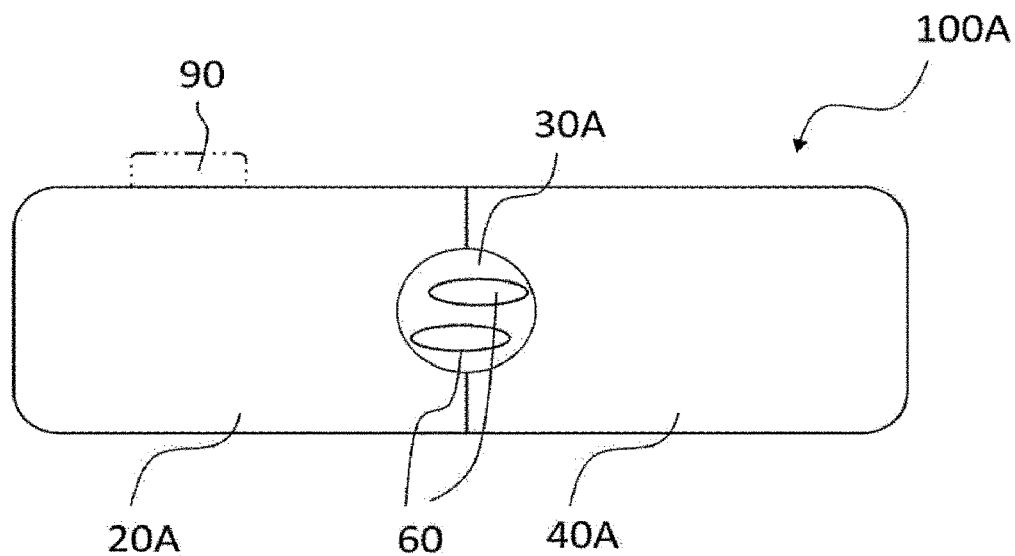
FIG. 1C shows a plan view of a modified example 100A of the first embodiment of the present invention. In the figure, the dashed-double-dotted line indicates the boundary line of the partition pattern on the bottom surface.

The modified example 100A of the first embodiment will be hereinafter described with reference to FIG. 1C. The components of the modified example 100A of the first embodiment and the usage thereof are the same as in the dish 100 of the first embodiment shown in FIGS. 1A and 1B, except that the partition pattern (partition shape) of the first, second, and third regions on the bottom surface is different. Accordingly, only the partition pattern will be described below, while the same parts as in the dish 100 of the first embodiment will be denoted by the same reference numerals, and the descriptions thereof will be omitted.

The modified example 100A of the first embodiment is the same as the dish 100 of the first embodiment in that the second region 30A is arranged at the boundary between the first region 20A and the third region 40A. However, the modified example 100A of the first embodiment is different from the dish 100 of the first embodiment in that the first region 20A and the third region 40A are in contact with each other.

The second region 30A can have various shapes as long as the shape is closed. In FIG. 1C, a substantially circular partition is formed, but there is no limitation to circular shapes, and substantially polygonal shapes (such as substantially quadrangular, substantially hexagonal, and substantially octagonal shapes) may be employed.

Lid 150 for Dish 100 of First Embodiment and Modified Example 100A Thereof The dish 100 of the first embodiment and the modified example 100A thereof may include the lid 150. Hereinafter, the lid 150 will be described with reference to FIGS. 1D and 1E.

Figure 1D:
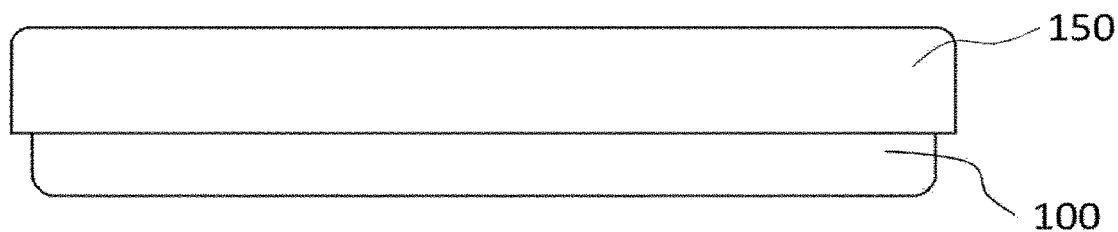
FIG. 1D shows a front view of the dish 100 of the first embodiment of the present invention covered with a lid 150.
Figure 1E:
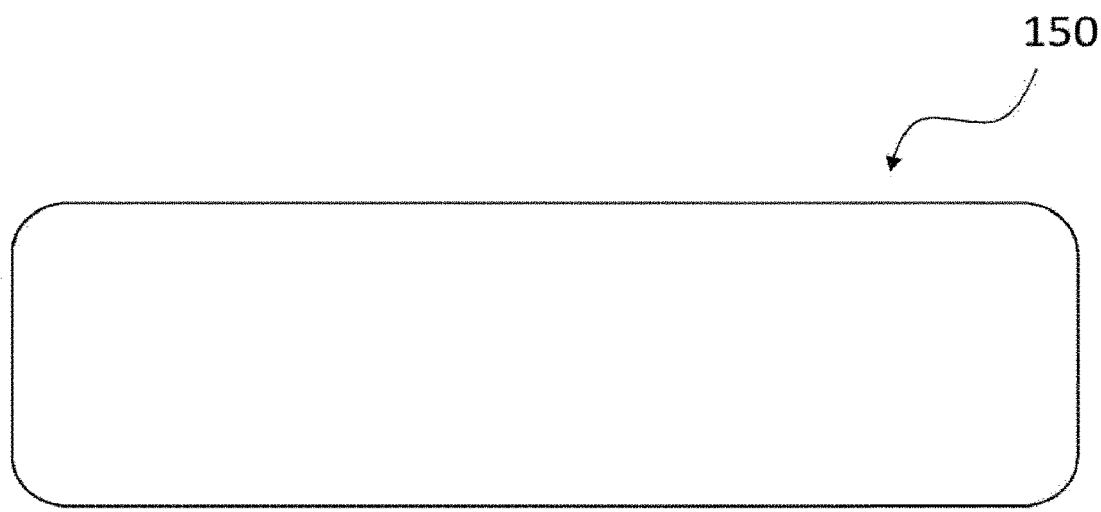
FIG. 1E shows a plan view of the lid 150.

As shown in FIGS. 1D and 1E, the lid 150 can be a lid that covers the upper surface of the dish 100. The shape of the lid 150 is not limited, as long as the lid 150 is a lid that covers the upper surface of the dish 100. It is preferable that the lid 150 be a lid that can cover the upper surface of the dish 100 and can block the air flow between the inside and the outside of the dish 100, for enhancing the accuracy of the behavior evaluation based on olfactory sense.

The tag 90 may be provided in the lid 150.
Usage of Lid 150

After the test sample and nematodes have been arranged, the lid 150 can be placed on the dish as a cover. Thereby, the influence of the outside air can be prevented, and the odor can be effectively confined inside the dish.

Modified Example 150A of Lid 150

Figure 1F:
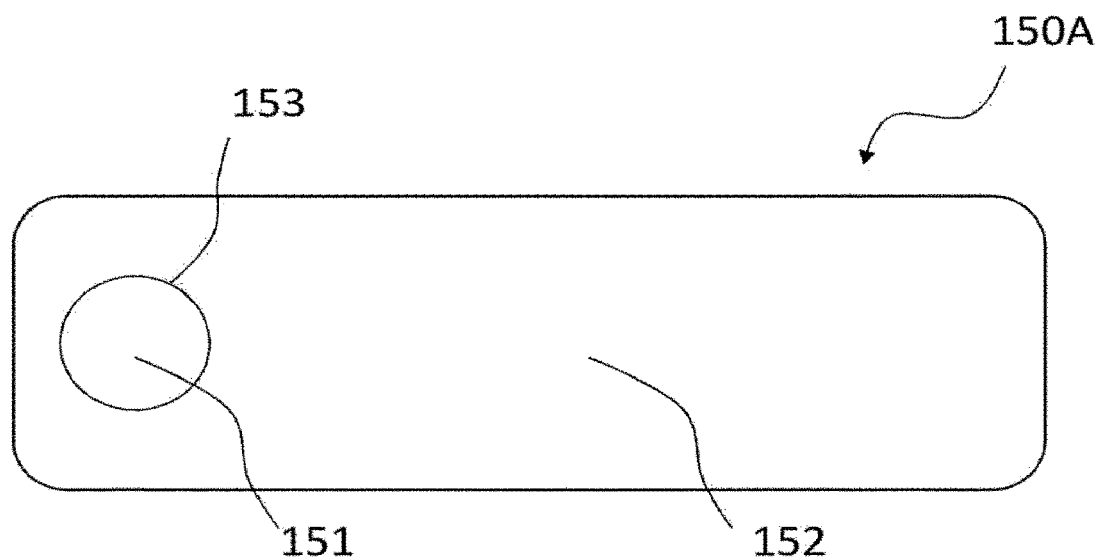
FIG. 1F shows a plan view of a modified example 150A of the lid 150.

The modified example 150A of the lid 150 will be hereinafter described with reference to FIGS. 1D and 1F. As shown in FIG. 1F, the components of the lid 150A and the usage thereof are the same as in the lid 150 except that the lid 150A includes a test sample seat 151. Accordingly, only the test sample seat 151 will be described below, while the same parts as in the lid 150 will be denoted by the same reference numerals, and the descriptions thereof will be omitted.

As shown in FIG. 1F, the lid 150A includes the test sample seat 151 on a surface opposed to the bottom surface of the dish when the lid is closed. The test sample seat 151 is formed in a region 1 to 3 cm away from the center of the lid 150A in the longitudinal direction. In FIG. 1F, the test sample seat 151 is shown to be circular, but there is no limitation to this. The test sample seat 151 can be substantially circular, substantially linear, or substantially quadrangular.

In one aspect, the test sample seat 151 has a boundary 153 between the test sample seat 151 and other regions 152. The boundary 153 can be formed by printing or forming an indented shape.

Figure 1G:
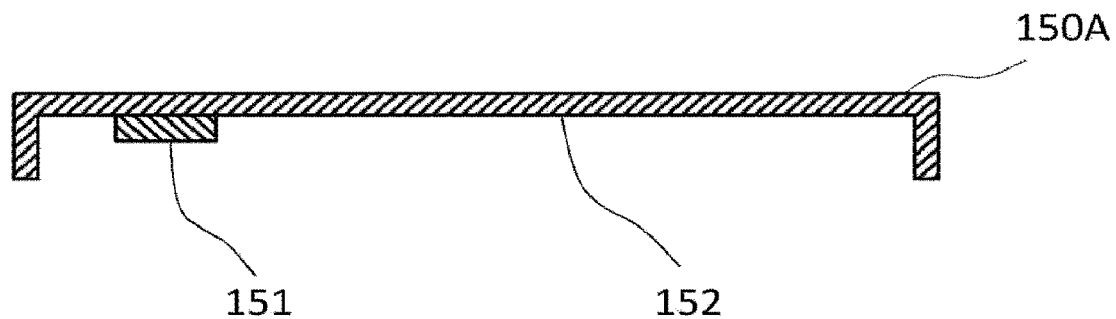
FIG. 1G shows a sectional view, taken along a straight line passing through 151, according to an aspect of the modified example 150A.
Figure 1H:
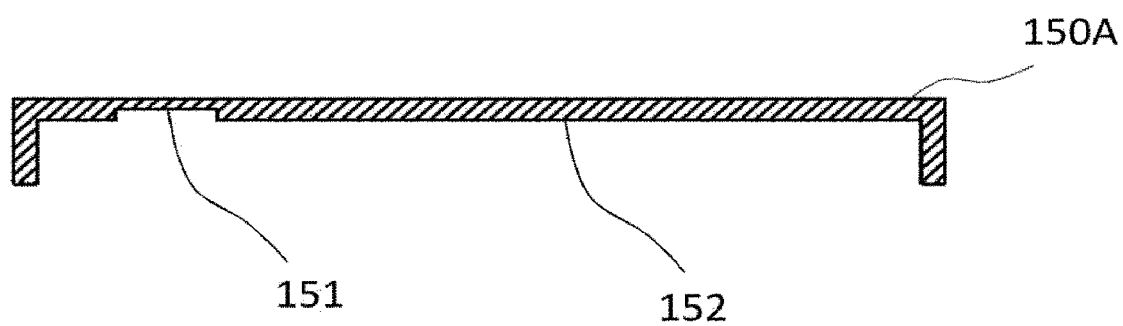
FIG. 1H shows a sectional view, taken along a straight line passing through 151, according to an aspect of the modified example 150A.
Figure 1I:
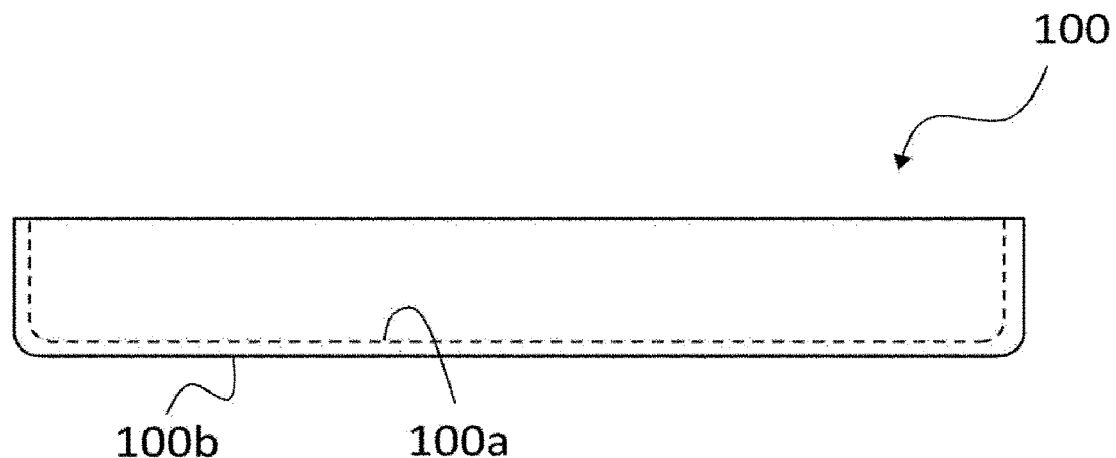
FIG. 1I shows a sectional view, taken along A-A, of the dish 100 of the first embodiment of the present invention (see FIG. 1A).

In one aspect, the test sample seat 151 and the other regions 152 have a step at the boundary 153. In one aspect, the test sample seat 151 may project more than the other regions 152 toward the bottom surface of the dish when the lid is closed, as shown in FIG. 1G. In one aspect, the test sample seat 151 may be recessed more than the regions 152 from the bottom surface of the dish when the lid is closed, as shown in FIG. 1H. As shown in FIG. 1G, in the case where the test sample seat 151 projects more than the other regions 152 toward the bottom surface of the dish when the lid is closed, the material of the test sample seat 151 may be the same as or different from the material of the regions 152 or the lid 150A.

In one aspect, the test sample seat 151 has a different hydrophilicity from that of the other regions 152 on the surface of the lid 150A opposed to the bottom surface of the dish when the lid is closed.

In one aspect, the test sample seat 151 has a hydrophilic surface, and the other regions 152 has a hydrophobic surface. Thereby, an aqueous test sample can be accurately arranged on the test sample seat 151. In one aspect, the test sample seat 151 has a hydrophobic surface, and the other regions 152 has a hydrophilic surface. Thereby, an oily test sample can be accurately arranged on the test sample seat 151.

Usage of Modified Example 150A of Lid

After the test sample and nematodes have been arranged, the lid 150A can be put on the dish. Thereby, the influence of the outside air can be prevented, and the odor can be effectively confined inside the dish.

In the case of using the lid 150A, the test sample can be arranged on the test sample seat 151 of the lid 150A, and nematodes can be arranged in the dish. In the evaluation of the taxic behavior through olfactory sense, the test sample and nematodes may be arranged spaced from each other, and even in such a case, the odor can diffuse through the air to reach the nematodes. Further, since the odor component of the test sample that is arranged on the test sample seat 151 of the lid 150A reaches the nematodes, this method is suitable for the evaluation of the taxic behavior, particularly, through olfactory sense. This method is particularly suitable, in the case where a test sample has a powerful chemotaxis, for evaluating the taxic behavior through olfactory sense with respect to the odor component of the test sample.

The test sample can be arranged in the lid 150A by introducing the test sample from beneath the lid with the surface that is opposed to the bottom surface of the dish when the lid 150A is closed facing downward. The test sample can be arranged in the lid 150A by introducing the test sample from beneath the lid with the surface that is opposed to the bottom surface of the dish when the lid 150A is closed facing upward and then turning the lid upside down.

Second Embodiment

The dish 200 of the second embodiment will be described with reference to FIG. 2A. The dish 200 of the second embodiment is the same as the dish 100 of the first embodiment shown in FIGS. 1A and 1B except that the partition pattern on the bottom surface is different. Accordingly, the same parts as in the dish 100 of the first embodiment will be denoted by the same reference numerals, and the descriptions thereof will be omitted.

Figure 2A:
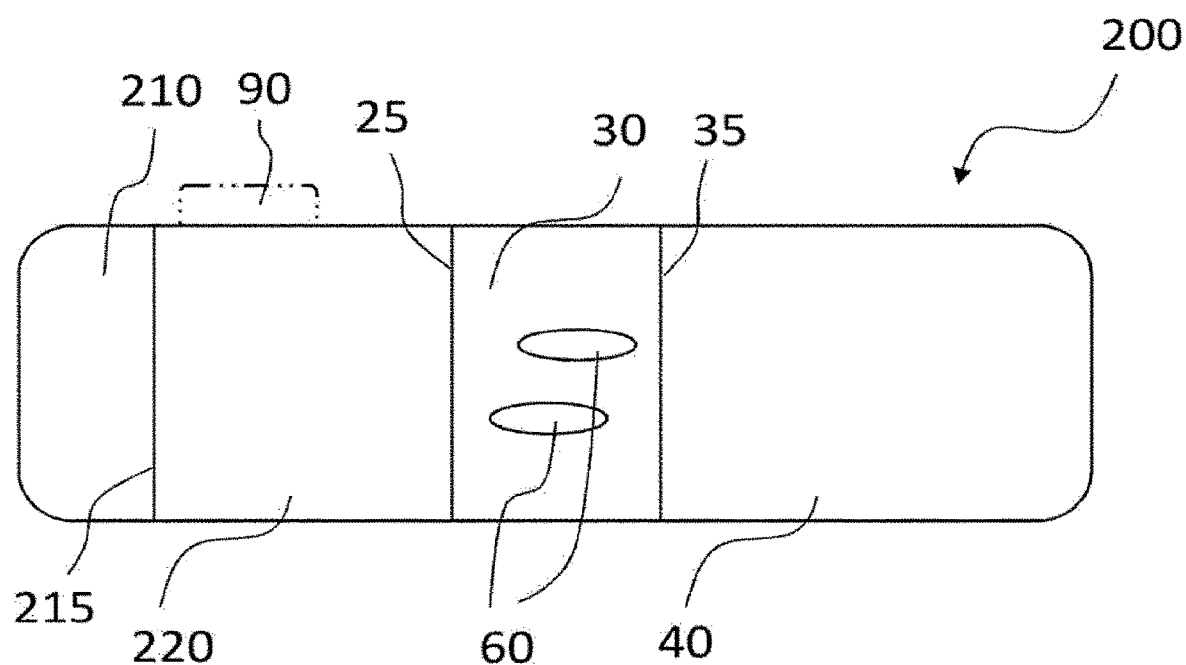
FIG. 2A shows a plan view of a dish 200 of the second embodiment of the present invention. In the figure, the dashed-double-dotted line indicates the boundary line of the partition pattern on the bottom surface.

As shown in FIG. 2A, the bottom surface of the dish 200 of the second embodiment is partitioned into at least four regions of a first region 210, a second region 220, a third region 30, and a fourth region 40 from an end on one side toward the other end in the longitudinal direction. The difference from the dish 100 of the first embodiment is that the first region 10 is further partitioned into two of the first region 210 and the second region 220 in the dish 200 of the second embodiment. As shown in FIG. 2A, the first region 210 and the second region 220 are separated from each other by a line 215 in the dish 200 of the second embodiment.

In the dish 200 of the second embodiment, the test sample can be arranged, for example, in the first region 210, on the line 215, or over both of them. Since the area in which the test sample is to be arranged is partitioned, the distance between the test sample and the nematodes 60 (which are applied to a part or the whole of the third region 30) is easily maintained constant in different tests. The first region 210 and the third region 30 can hold a distance, for example, of about 1 cm to 3 cm, about 1 cm to 2 cm, about 1.5 cm to 2.5 cm, or about 1.5 cm to 2 cm.

Modified Example 200A of Second Embodiment

Figure 2B:
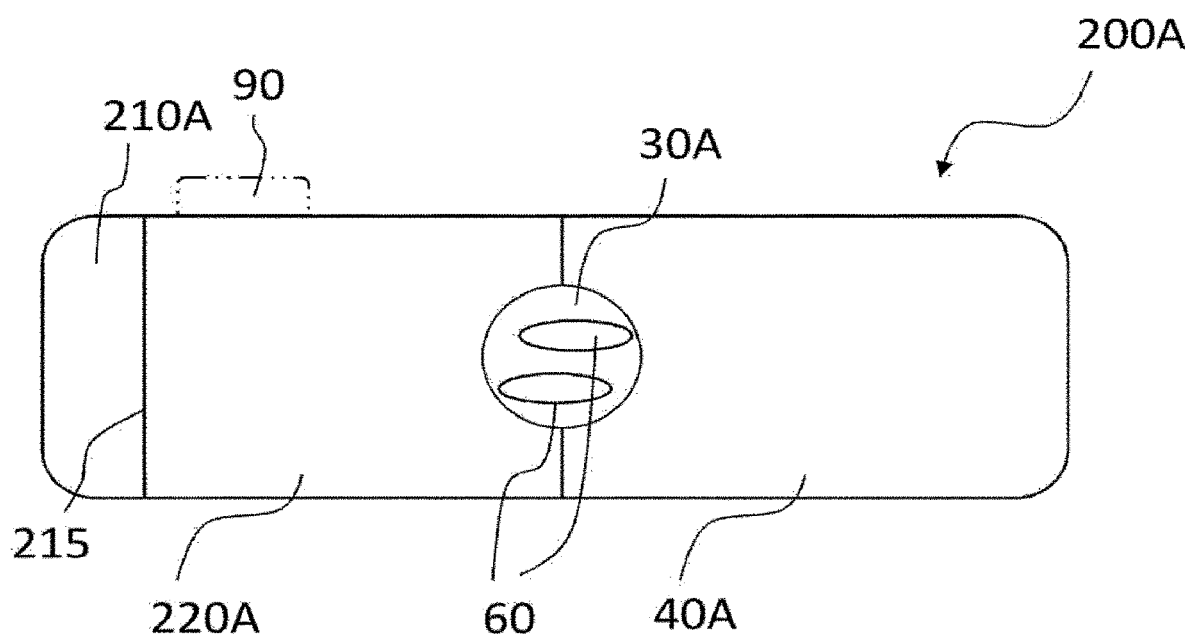
FIG. 2B shows a plan view of a modified example 200A of the second embodiment of the present invention. In the figure, the dashed-double-dotted line indicates the boundary line of the partition pattern on the bottom surface.

The modified example 200A of the second embodiment will be hereinafter described with reference to FIG. 2B. The components of the modified example 200A of the second embodiment are the same as in the dish 200 of the second embodiment shown in FIGS. 2A and 1B except that the partition pattern (partition shape) on the bottom surface is different. Accordingly, only the partition pattern will be described below, while the same parts as in the dish 200 of the second embodiment will be denoted by the same reference numerals, and the descriptions thereof will be omitted.

The modified example 200A of the second embodiment is the same as the dish 100 of the first embodiment in that the third region 30A is arranged at the boundary between the second region 220 and a fourth region 40A. However, the modified example 200A of the second embodiment is different from the dish 200 of the second embodiment in that the second region 220 and the fourth region 40A are in contact with each other.

The third region 30A can have various shapes as long as the shape is closed. In FIG. 2B, a substantially circular partition is formed, but there is no limitation to circular shapes, and substantially polygonal shapes (such as substantially quadrangular, substantially hexagonal, and substantially octagonal shapes) may be employed.

Hereinabove, the dish of the present invention has been described for each embodiment, but the bottom surface may be further finely partitioned in such a dish. Any partition may be employed, as long as humans or machines can distinguish the at least three regions from one another.

Multipanel of the Present Invention

Hereinafter, a multipanel of the present invention will be described with reference to FIG. 3.

Figure 3B:
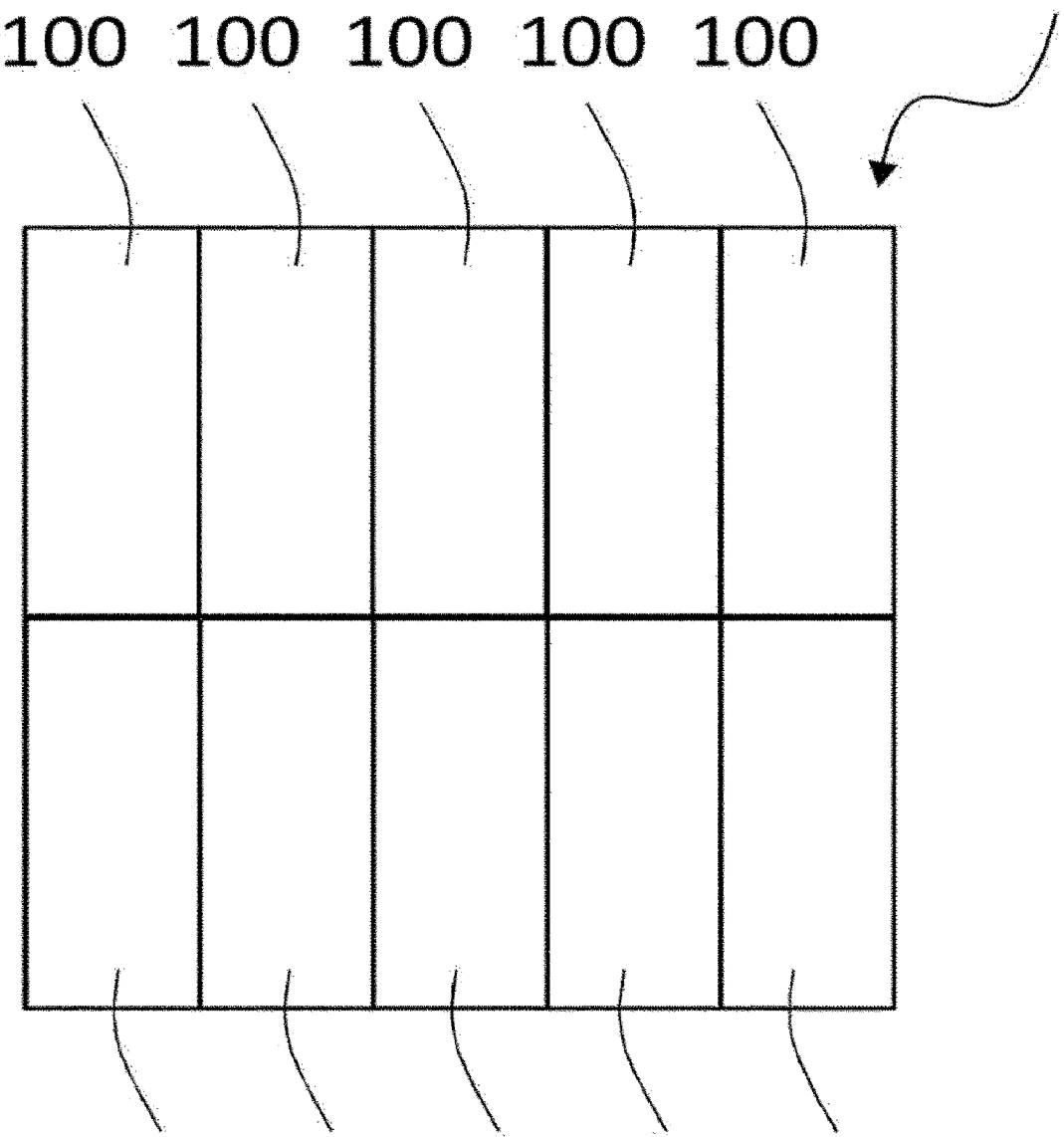
FIG. 3B shows a plan view of an example 500A of the multiplate of the present invention.
Figure 3C:
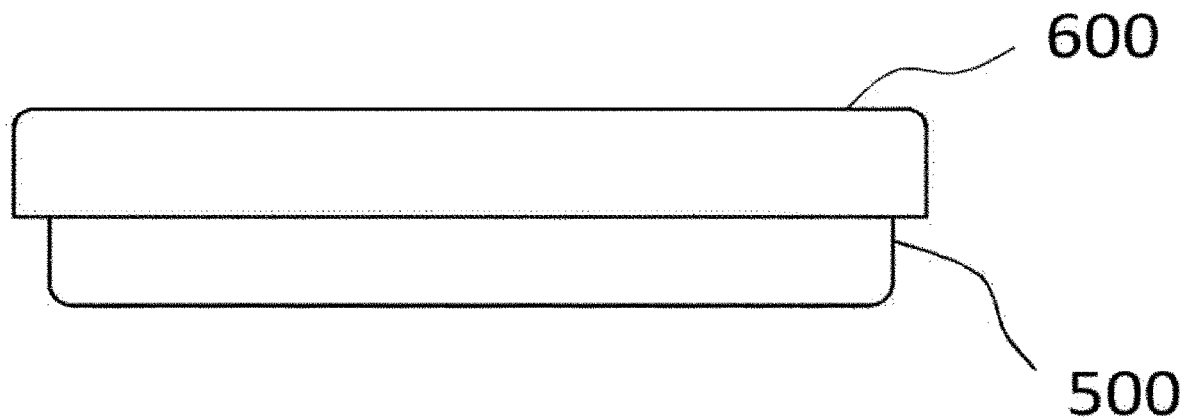
FIG. 3C shows a front view of the example 500 of the multiplate with a lid 600 of the present invention.

As shown in FIG. 3A, a multipanel 500 of the present invention can be an assembly of dishes 100 of the first embodiment of the present invention arranged vertically or horizontally. Further, as shown in FIG. 3B, a multipanel 500A of the present invention can be an assembly of dishes 100 of the first embodiment of the present invention arranged vertically and horizontally. In the multipanel 500 or 500A of the present invention, 2 to 1000, 4 to 700, 6 to 600, 8 to 500, or 10 to 300 dishes 100 of the first embodiment of the present invention, for example, may be arranged, though there is no specific limitation thereto.

Further, in such a multipanel, adjacent dishes 100 of the first embodiment may be connected to each other directly or via a spacer.

Although the dish 100 of the first embodiment is used as a dish in the example shown in FIGS. 3A and B, the dish 200 of the second embodiment, the modified example 100A of the first embodiment, or the modified example 200A of the second embodiment may be used as a dish.

The multipanel 500 or 500A of the present invention may further have the lid 600. It can be expected to further effectively prevent the leakage of the test sample in each dish into its adjacent dishes by the lid 600 and the sidewall of each dish. The lid 600 may include the test sample seat 151 like the lid 150A. Since the usage of the lid 600 is as described above for the lid 150 and the lid 150A, the description thereof is omitted.

Third Embodiment

The third embodiment provides a solution to a new problem that the number of nematodes that penetrate into the gap between the inner wall of the dish and the solid medium increases as the size of the dish decreases, and the number of nematodes that can be observed decreases as time elapses. The third embodiment is characterized by the shape of the surface (upper surface) of the solid medium that is formed after the solid medium is introduced into the dish, not by the shape of the dish. Hereinafter, the third embodiment will be described with reference to FIGS. 10 to 12.

Figure 10:
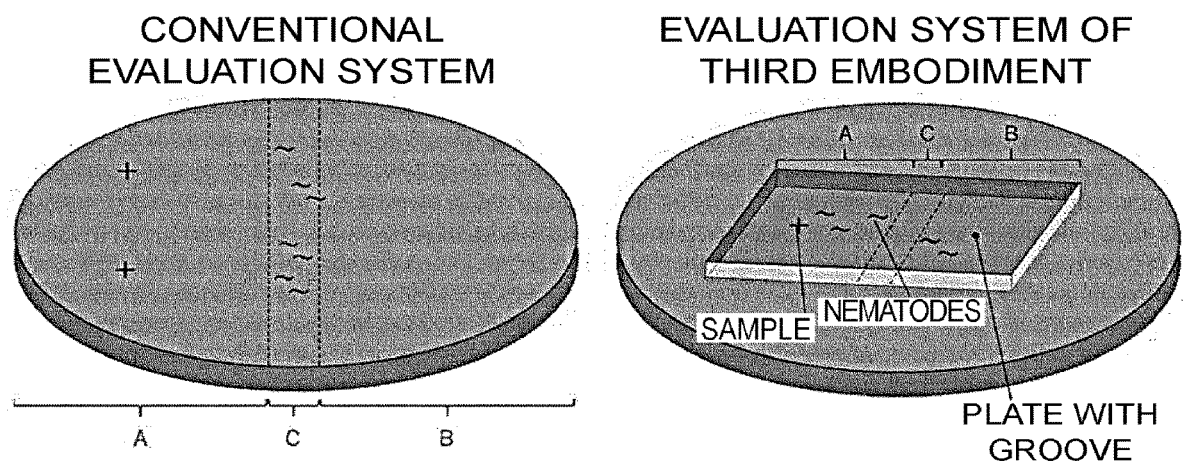
FIG. 10 is a schematic diagram comparing the evaluation system of the third embodiment of the present invention with a conventional evaluation system for the taxic behavior of nematodes. In this evaluation system in which a test sample is arranged at the position shown by the symbol "+", and nematodes are arranged in the region shown by the symbol "C", it is understood that the nematodes show attraction behavior in the case of moving toward "A", and the nematodes show avoidance behavior in the case of moving toward "B".

FIG. 10 is a schematic diagram comparing the evaluation system of the third embodiment of the present invention with the conventional evaluation system disclosed in Patent Literature 1. In the conventional evaluation system, the outer periphery of the surface onto which nematodes are disseminated is surrounded by the sidewall of the dish. The evaluation system of the third embodiment of the present invention has a planar recess on the surface of the solid medium in the evaluation system, and the taxic behavior is evaluated inside the recess. Since the taxic behavior of nematodes is observed while the recess is covered with a lid so that nematodes are confined within the recess, the recess may be referred to as "behavior observation plane" in this description.

Figure 11A:
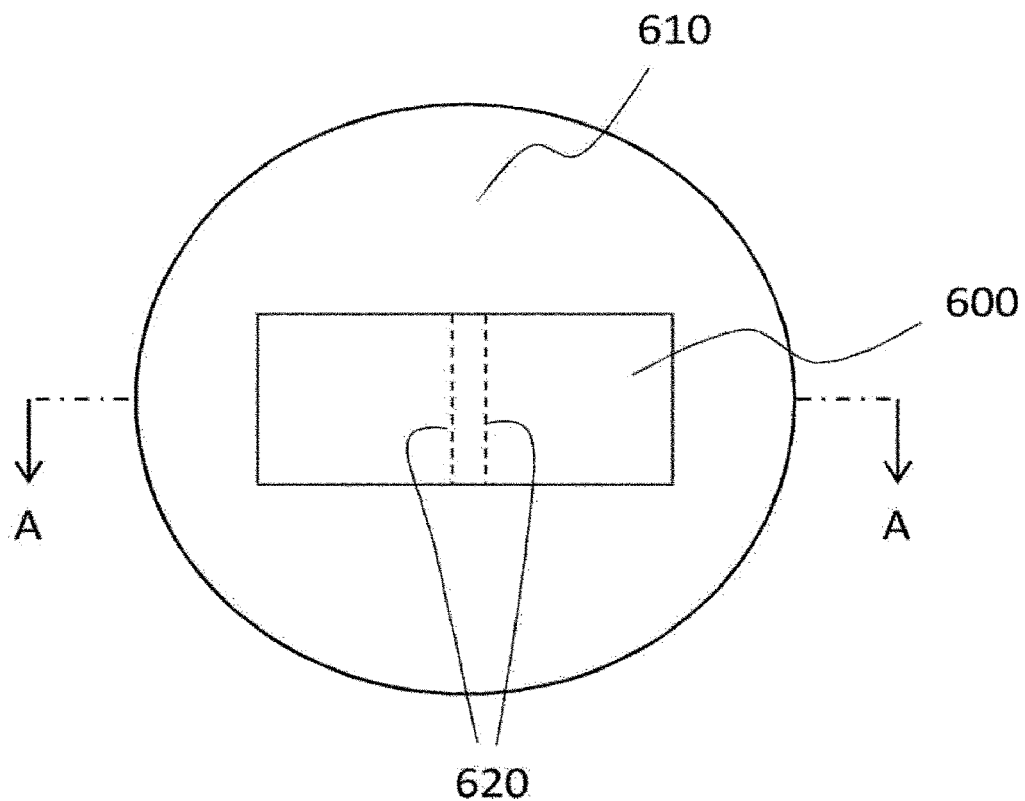
FIG. 11A is a plan view showing a surface of a solid medium in the evaluation system of the third embodiment of the present invention.
Figure 11B:
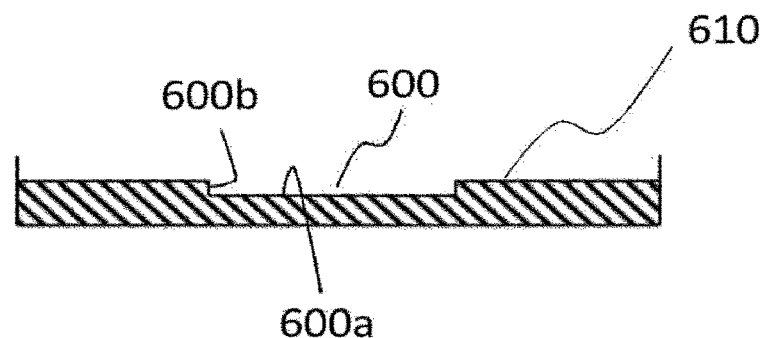
FIG. 11B is a sectional view, taken along A-A, showing the surface of the solid medium in the evaluation system of the third embodiment of the present invention.

As shown in FIG. 11, a solid medium surface 610 in the third embodiment has a substantially rectangular planar recess 600. The substantially rectangular planar recess 600 has a recess bottom surface 600a and a recess side surface 600b. The recess bottom surface 600a can have a length in the longitudinal direction within the range of 3 cm to 6 cm and a length in the transverse direction within the range of 1 cm to 3 cm or 3 cm to 6 cm. The length of the recess bottom surface 600a in the longitudinal direction can be preferably 4 cm to 6 cm, preferably 4.5 cm to 5.5 cm, preferably 5 cm. The length of the recess bottom surface 600a in the transverse direction can be preferably 1.5 cm to 2.5 cm, preferably 2 cm. Alternatively, the length in the transverse direction can be preferably 3.5 cm to 5.5 cm, preferably 4 cm to 5 cm. Further, the length of the recess in the longitudinal direction may be 4.5 cm to 5.5 cm, and the length of the recess in the transverse direction may be 4.5 cm to 5.5 cm. The depth (thickness) of the recess 600 or the height of the recess side surface 600b is equal to or greater than the thickness of the nematodes and can be 5 mm or less, 4 mm or less, 3 mm or less, 2 mm or less, preferably 1 mm or less, more preferably 0.5 mm or less, further preferably 0.3 mm or less, furthermore preferably 0.2 mm or less, for example, about 0.1 mm. The depth is preferably set to a depth of the thickness of the nematodes used for behavior observation+about 10 to 50%, a depth of the thickness of the nematodes+about 10 to 40%, a depth of the thickness of the nematodes+about 10 to 30%, or a depth of the thickness of the nematodes+about 10 to 20%, since both the purpose of confining the nematodes within the behavior observation plane and the purpose of allowing the nematodes to move within the behavior observation plane can be achieved.

For facilitating microscopy, the recess bottom surface 600a is desirably a substantially flat surface. This facilitates observation of the entire behavior observation plane with the focus of the microscope being constant.

Further, the recess 600 can be completely covered with a lid 650 during the behavior observation so that the nematodes do not escape outside the recess 600. Further, the depth of the recess 600 can be approximated to the thickness of the nematodes (such as about 0.1 mm) in the present invention. Thereby, when the recess 600 is covered with a plate 650, the nematodes adhering to an inner wall 650a of the plate 650 can be observed like the nematodes adhering to the bottom surface 600a of the recess 600, as well as making it difficult for the nematodes to escape outside the recess 600.

Figure 11C:
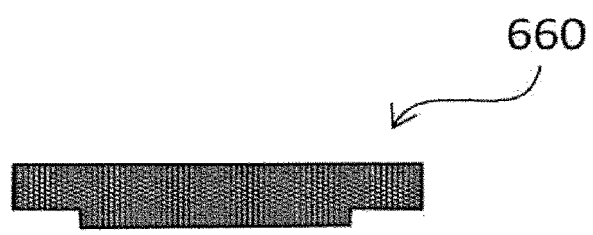
FIG. 11C is a sectional view of a mold to form a recess.

Conventionally, nematodes penetrate into the gap between the sidewall and the solid medium upon reaching the sidewall of the evaluation system, and the nematodes that have penetrated therein could not be used for behavior evaluation. In the present invention, the inner surface of the recess 600 is smoothly shaped. Being smoothly shaped means that there are neither gaps nor holes into which nematodes can penetrate. Such a recess having a surface that is smoothly shaped can be produced by introducing a culture medium melted by heating, which is to be solidified upon cooling, into a dish and applying a mold having the shape of the recess 600 to the molten culture medium before solidification from above, followed by cooling. The mold having the shape of the recess 600 can be a mold 660 having a complementary shape to the shape of the recess 600, for example, as shown in FIG. 11C.

Here, the dish may be provided with two lines 620 (marks) showing the center region when the recess bottom surface 600a is observed from above. The nematodes can be arranged in the region shown by the lines 620, and the test sample can be arranged in either of the regions outside the two lines 620 (or the test sample may be arranged on the lid). That is, the bottom surface 600a (behavior observation plane) of the recess 600 has at least two partition lines 25 and 35 as marks, so that the bottom surface area is partitioned into at least three regions from an end on one side toward the other end in the longitudinal direction, as in the first embodiment or the second embodiment. Thereby, the bottom surface is partitioned into at least three regions of the first region 20, the second region 30, and the third region 40, and the second region 30 is particularly arranged at the boundary between the first region 20 and the third region 40. The partition lines do not physically divide the area, and it is sufficient if the partition lines serve as marks to distinguish the boundaries between different regions.

Figure 12A:
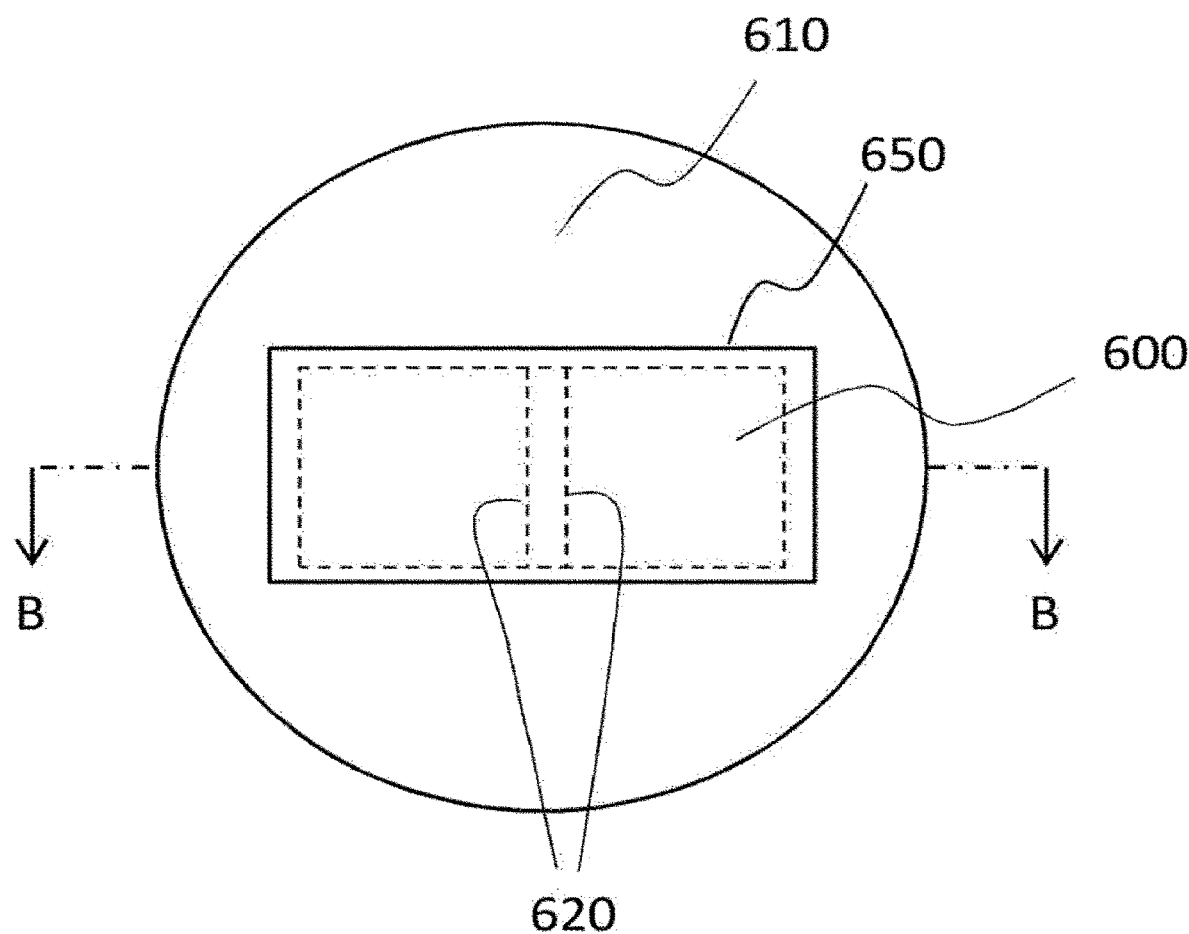
FIG. 12A is a plan view of the evaluation system of the third embodiment of the present invention.
Figure 12B:
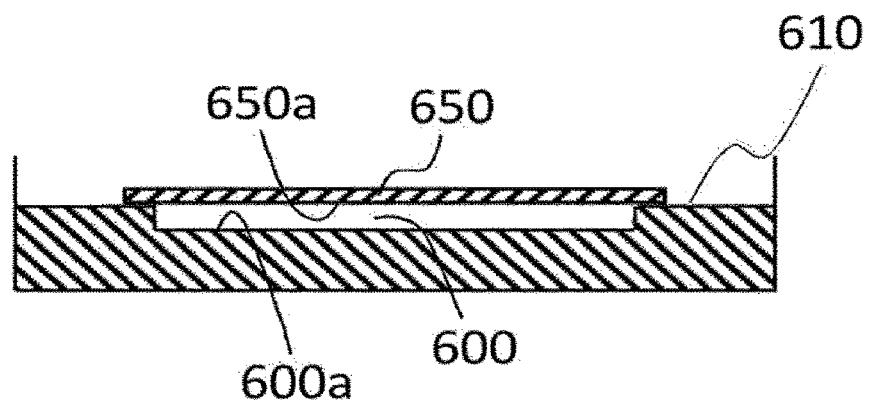
FIG. 12B is a sectional view, taken along B-B, of the evaluation system of the third embodiment of the present invention.

As shown in FIG. 12, the recess 600 is covered with the plate 650 that covers the entire recess during the assay. The plate 650 is flat. The plate 650 may be optically non-transparent, in the case where the dish is optically transparent, but can be optically transparent. It is advantageous that the plate 650 is optically transparent, since nematodes can be observed using a microscope from above, in the state where the recess 600 is covered with the plate 650. In the case where the plate 650 is not optically transparent, the dish is preferably optically transparent, since nematodes can be observed using an inverted microscope from beneath the dish in this case. In the case where neither the plate nor the dish is optically transparent, nematodes adhering to the recess and/or the plate can be observed by detaching the plate in observation.

The partition lines 620 may be provided on the bottom surface of the dish or may be provided on the upper surface or the lower surface 650a of the plate 650.

The present invention provides a combination of a dish, the plate 650 that covers the recess 600, and the mold 660 for producing the recess 600, in order to produce the behavior evaluation system of the third embodiment. In the combination, the dish may have the same partition pattern as the partition pattern on the bottom surface of the dish 100 of the first embodiment, the modified example 100A, the dish 200 of the second embodiment, or the modified example 200A, at a position corresponding to the shape of the recess 600 immediately below the portion where the recess 600 is formed. Further, the plate 650 that covers the recess 600 may have the same partition pattern as the partition pattern on the bottom surface of the dish 100 of the first embodiment, the modified example 100A, the dish 200 of the second embodiment, or the modified example 200A at a position corresponding to the recess 600 when covering the recess 600. Thus, the position where nematodes are arranged can be made stable, and attraction behavior and avoidance behavior are easily distinguished from each other.

Method for Evaluating Taxic Behavior of Nematodes Through Olfactory Sense in the Present Invention Hereinafter, a method for evaluating the taxic behavior of nematodes through olfactory sense will be described.

The present invention provides a method for evaluating the taxic behavior of nematodes in response to odor of a test sample, the method including:

a) providing a dish in which a test sample is arranged, and nematodes are arranged in a region or a site on the bottom surface 1 cm to 3 cm away from the test sample;

b) observing the arrangement of the nematodes at 3 to 15 minutes after dissemination; and c) evaluating whether the nematodes show attraction behavior or avoidance behavior in response to the test sample, from the arrangement of the nematodes observed.

Hereinafter, each of steps a) to c) will be described.

a) Providing a Dish in which a Test Sample is Arranged, and Nematodes are Arranged in a Region or a Site on the Bottom Surface 1 cm to 3 cm Away from the Test Sample In a), the dish in which the test sample is arranged is used. The dish may have no lid but preferably can have a lid. A solid medium for nematodes can be added to the dish. As the solid medium for nematodes, a solid medium for culturing or growing nematodes can be used. As the solid medium, a well-known culture medium, for example, an agar medium can be used. The test sample is not specifically limited but can be preferably arranged on the bottom surface of the dish, particularly, near the periphery of the bottom surface of the dish. Alternatively, the test sample is not specifically limited but can be preferably arranged on the surface (or the lower surface) of the lid of the dish that is opposed to the bottom surface of the dish, particularly, near the periphery of the lower surface of the lid. Since the test sample is arranged on the bottom surface of the dish or the periphery of the lid (that is, near the sidewall), a certain distance or more is easily ensured from the test sample when nematodes are arranged at the center of the bottom surface of the dish.

The distance from the site where the test sample is arranged to the site where the nematodes are disseminated can be about 1 cm to 3 cm, about 1 to 2.5 cm, about 1.5 to 2 cm, about 1.5 cm to 2.5 cm, or about 2 cm.

The number of nematodes disseminated can be, for example, about 10 to 500, for example, about 100 to 500.

As the test sample, any sample can be used. Examples of the test sample include samples of subjects (such as humans) suspected to be suffering from cancer. The test sample can be, for example, cells suspected to be cancer cells, tissues suspected to be cancer tissues, or extracts or lysates of these, or can be samples of body fluids, such as blood (for example, blood plasma) or urine, of subjects suspected to be suffering from cancer.

The evaluation of taxic behavior of nematodes through olfactory sense can be performed, for example, as described in WO 2015/088039.

In conventional methods, a nematicide (such as sodium azide) needs to be arranged in the dish provided in a) near the test sample and in a region opposite to the test sample as seen from the position where nematodes are arranged, but the method of the present invention does not require to use a nematicide.

The dish, provided in a), in which a test sample is arranged, and nematodes are arranged in a region or a site 1 cm to 3 cm away from the test sample may be obtained by arranging the nematodes after the test sample is arranged or may be obtained by arranging the test sample after the nematodes are arranged. In the case where the test sample is arranged after the nematodes are arranged, the test sample may be arranged after the nematodes are arranged in the site where the nematodes are to be arranged and are cultured to be grown.

Since the possibility that the nematodes widely diffuse on the bottom surface increases if time elapses after the nematodes are arranged, observation is desirably started immediately after the nematodes are arranged. Accordingly, it is preferable that counting the time of 3 to 15 minutes in b), which will be described below, be started immediately after the test sample is arranged at a predetermined position of the dish, and then the nematodes are arranged at a predetermined position. In the case where the test sample is arranged after the nematodes are arranged, it is desirable that the test sample be arranged preferably within 3 minutes, more preferably within 1 minute from the nematodes are arranged.

As to the place where the nematodes are arranged in the dish provided in a), the nematodes are preferably arranged in a region 0.5 cm or more spaced from the sidewalls of both the dish and the lid (however, it is not excluded to arrange the nematodes in a region within 0.5 cm from the sidewalls).

b) Observing the Arrangement of the Nematodes on the Bottom Surface at 3 to 15 Minutes after the Test Sample and the Nematodes are Arranged in the Dish In b), the nematodes show taxic behavior immediately after the test sample is arranged in the dish (or upon the nematodes being arranged in the dish in which the test sample is arranged). After a lapse of about 3 to 15 minutes, preferably 3 to 12 minutes, more preferably 5 to 10 minutes, for example, 5 minutes, 7.5 minutes, or 10 minutes, the nematodes can move over a distance enough to evaluate the taxic behavior. Therefore, the arrangement of the nematodes on the bottom surface can be observed after a lapse of about 3 to 15 minutes, preferably 3 to 12 minutes, more preferably 5 to 10 minutes, for example, 5 minutes, 7.5 minutes, or 10 minutes, from the time when the later one of the test sample or the nematodes is arranged, so that the taxic behavior of nematodes can be evaluated. The taxic behavior of nematodes is enhanced to such an extent to be sufficiently visualized by setting the time to 3 minutes or more, and thus the accuracy in evaluating the taxic behavior is improved. Further, when the time is 15 minute or less, the possibility that the nematodes start to move on the dish at random due to sensitization occurring in olfactory sense in nematodes decreases, and thus the accuracy of the taxic behavior is improved. In the case where the nematodes are arranged on the bottom surface of the dish, and the test sample is arranged on the lid, the "time when the test sample and the nematodes are arranged in the dish" means the time when the dish is covered with the lid.

c) Evaluating Whether the Nematodes Show Attraction Behavior or Avoidance Behavior in Response to the Test Sample, from the Arrangement of the Nematodes Observed In c), whether the nematodes show attraction behavior or avoidance behavior, or neither attraction behavior nor avoidance behavior, in response to the test sample can be evaluated from the arrangement of the nematodes observed. In c), in the case where the proportion of the nematodes that approach the test sample is higher than the proportion of the nematodes that move away from the test sample, the nematodes can be evaluated to show attraction behavior in response to the test sample. Further, in the case where the proportion of the nematodes that approach the test sample is lower than the proportion of the nematodes that move away from the test sample, the nematodes can be evaluated to show avoidance behavior in response to the test sample in c). In the case where the proportion of the nematodes that approach the test sample is equivalent to the proportion of the nematodes that move away from the test sample, the nematodes may be evaluated to show neither attraction behavior nor avoidance behavior in c).

Further, whether the nematodes show attraction behavior or avoidance behavior may be evaluated in c), for example, by determining a taxis index using the following formula.

Taxis Index (Taxis index)={(the number of nematodes in region indicated by O-mark)−(the number of nematodes in region indicated by X-mark)}/the number of all nematodes The taxis index takes a numerical value ranging from −1 to +1, where the value is positive in the case of showing attraction behavior, and the value is negative in the case of showing avoidance behavior. Further, a larger absolute value of the numerical value can be interpreted as the taxis being shown more strongly.

It is also possible that c) further includes evaluating whether the test sample is an attractant or a repellent, or neither an attractant nor a repellent, based on the taxic behavior shown by the nematodes in response to the test sample.

The inventors have revealed in WO 2015/088039 that nematodes show attraction behavior in response to body fluids (such as urine) of cancer patients, while showing avoidance behavior in response to body fluids (such as urine) of healthy individuals. It is understood that this is based on the fact that factors specific to cancer, which are released from cancer cells or cancer tissues of cancer patients into body fluids of cancer patients, induce the attraction behavior of nematodes.

Accordingly, in the present invention, the test sample can be cells suspected to be cancer cells, tissues suspected to be cancer tissues, or extracts or lysates of these, or in the case of using samples of body fluids such as blood (for example, blood plasma) or urine of subjects (such as humans) suspected to be suffering from cancer, whether the sample contains attractants derived from cancer can be determined based on the taxic behavior of nematodes. Further, the results for the determination are useful as a piece of the basic information used when doctors make a diagnosis of cancer and help the diagnosis of cancer by doctors.

Accordingly, another aspect of the present invention provides a method for determining whether the test sample contains an attractant derived from cancer, the method including a) to c) described above, and further including determining whether the test sample contains an attractant derived from cancer, based on the taxic behavior of nematodes.

Still another aspect of the present invention provides a method for making a diagnosis whether a subject is suffering from cancer, the method including: obtaining a test sample from the subject; a) to c) described above; and d) evaluating the subject as suffering from cancer in the case where the nematodes show attraction behavior in response to the test sample, or evaluating the subject as not suffering from cancer in the case where the nematodes show avoidance behavior in response to the test sample.

In the method for evaluating the taxic behavior of nematodes in response to odor of a test sample, the method for determining whether a test sample contains an attractant derived from cancer, and the method for making a diagnosis whether a subject is suffering from cancer of the present invention, the taxic behavior of nematodes through olfactory sense is evaluated, but there is no need of using nematicides (for example, dangerous medicines such as sodium azide) for stopping the movement of the nematodes. Strict management is required for storing or using dangerous medicines such as sodium azide (such a constraint exists), and therefore the method of the present invention without using such dangerous medicines is useful in that one of the constraints on the implementation can be eliminated.

In the method for evaluating the taxic behavior of nematodes in response to odor of a test sample, the method for determining whether a test sample contains an attractant derived from cancer, and the method for making a diagnosis of whether a subject is suffering from cancer of the present invention, the dish or the behavior evaluation system of the present invention described above can be used, or the multiplate can be also used. The methods for using the dish, the behavior evaluation system, and the multiplate of the present invention in the methods of the present invention are as described above.

EXAMPLES

Example 1: Construction of System for Evaluating Taxic Behavior of Nematodes Using Olfactory Sense In this example, an attempt to construct a new system for evaluating the taxic behavior of nematodes was made.

Figure 4:
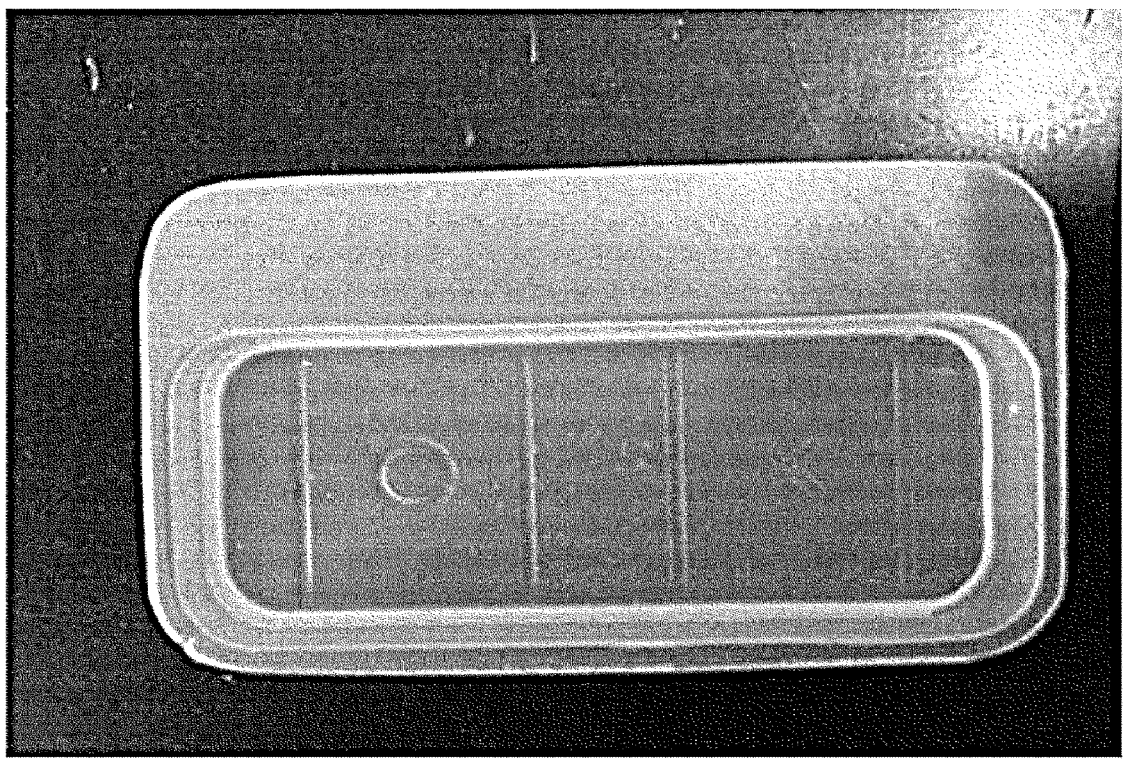
FIG. 4 shows an image of a 5 cm×2 cm rectangular dish prepared in this example. In the image, nematodes are shown by white thin points.

First, a rectangular dish having a bottom surface of 5 cm×2 cm was fabricated as an example (see FIGS. 1A and B). The image of the dish actually fabricated was as shown in FIG. 4. Nematodes were disseminated into a region defined by two lines at the center of the rectangular dish in the longitudinal direction, and an attractant or a repellent was applied to the region at the left end. Thus, attraction behavior in response to an attractant or avoidance behavior in response to a repellent of the nematodes were observed. In this example, isoamyl alcohol was used as an attractant, and nonanone was used as a repellent. Specifically, isoamyl alcohol was diluted 1000-fold with water, and 1 µL thereof was applied to the region at the left end. Further, 1 µL of the stock solution of nonanone was applied to the region at the left end. As the nematodes, wild type *C. elegans* (10 to 50 nematodes/experiment) were used.

For each of attraction behavior and avoidance behavior of nematodes, the taxis index described below was determined to investigate the sensitivity of the evaluation system constructed. Specifically, the difference in the number of nematodes between those moved to the region (region indicated by O-mark in FIG. 4, corresponding to region 1 of the first embodiment) located between the region at the left end to which an attractant or a repellent was applied and the region at the center in the longitudinal direction in which the nematodes were disseminated and those moved to the region on the opposite side (region indicated by X-mark in FIG. 4, corresponding to region 2 of the first embodiment) was determined, and the result was divided by the number of all nematodes to determine the taxis index.

Taxis Index (Taxis index)={(the number of nematodes in region indicated by symbol "O")−(the number of nematodes in region indicated by symbol "X")}/the number of all nematodes The experiment was repeated 5 times, to determine the average of taxis indices and SEM.

Figure 5:
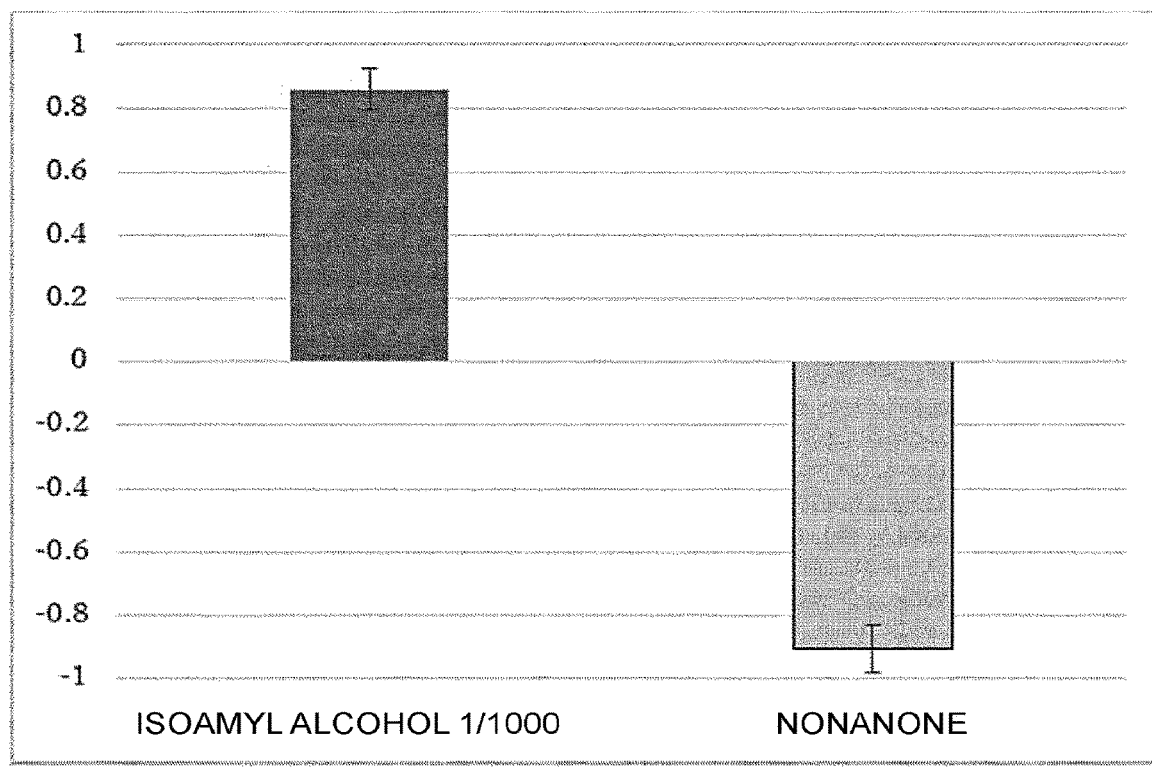
FIG. 5 is a graph showing that attraction behavior toward an attractant (isoamyl alcohol) and avoidance behavior from a repellent (nonanone) can be measured with high-sensitivity using the dish of the present invention.

The results were as shown in FIG. 5. FIG. 5 shows the taxis index assayed at only 10 minutes after the dissemination of the nematodes and standard errors (SEM). As shown in FIG. 5, a taxis index of over 0.8 in response to isoamyl alcohol that is an attractant was shown in the assay only for 10 minutes. This result indicates that 90% or more of the nematodes could be assayed as showing attraction behavior in response to the attractant within such a short period.

Further, a taxis index of below −0.8 in response to nonanone that is a repellent was shown. This result indicates that 90% or more of the nematodes could be assayed as showing avoidance behavior in response to the repellent within such a short period of time.

In the evaluation of the taxic behavior using olfactory sense, there may be cases where the evaluation is carried out for the purpose of determining whether the test substance is an attractant or a repellent, or neither an attractant nor a repellent. It turned out that whether the test substance is an attractant or a repellent could be determined within a short assay time with a surprising sensitivity by using the evaluation system of the present invention.

Conventionally, the taxic behavior based on olfactory sense has been evaluated using a 9 cm circular dish. In this case, the movable area of the nematodes is wide, and it is known that sensitization occurs in olfactory sense during movement so that nematodes come not to show immediate taxic behavior and move around at random. Poisons such as sodium azide are applied to the destination region as a countermeasure to prevent the nematodes that have once moved from further moving around at random.

Meanwhile, the evaluation system of the present invention enabled the taxic behavior of nematodes based on olfactory sense to be assayed with ultra-high sensitivity without using poisons. In the present invention, there was no need to use sodium azide, which had been conventionally indispensable to observe the taxic behavior based on olfactory sense.

Further, in conventional evaluation systems, nematodes have needed to move over a period of 30 minutes or more for evaluating the taxic behavior of nematodes. In contrast, in the evaluation system of the present invention, not only nematodes needed to move only for a fraction of the conventional time or less for the evaluation, but also the taxic behavior could be evaluated with higher sensitivity than in conventional systems.

In this example, the evaluation with high accuracy could be achieved by arranging the test sample and the nematodes closer to each other than in conventional systems. The reason why the taxic behavior was evaluated with high accuracy by the evaluation method of the present invention is considered that behavioral abilities of nematodes (which are influenced, for example, by the nutritional status, the environment temperature, the culture conditions, and the growth steps) had influenced the taxic behavior evaluation based on olfactory sense, as big noise which cannot be ignored (though such influence itself has not been known before the present invention), and the evaluation method of the present invention could minimize the influence.

Example 2: Evaluation of Taxic Behavior of Nematodes Through Olfactory Sense Using Urine of Cancer Patients It has been demonstrated that wild type nematodes show attraction behavior in response to urine of cancer patients and show avoidance behavior in response to urine healthy individuals. In this example, the taxic behavior in response to urine derived from a cancer patient was evaluated using a new evaluation system constructed in Example 1.

The taxic behavior was evaluated in the same manner as in Example 1 except that urine (1/20 dilution) of a cancer patient or urine (1/20 dilution) of a healthy individual was used as an attractant or a repellent. The assay time was set to 5 minutes or 10 minutes after the dissemination of nematodes based on the results of Example 1. The results were as shown in FIG. 6.

Figure 6:
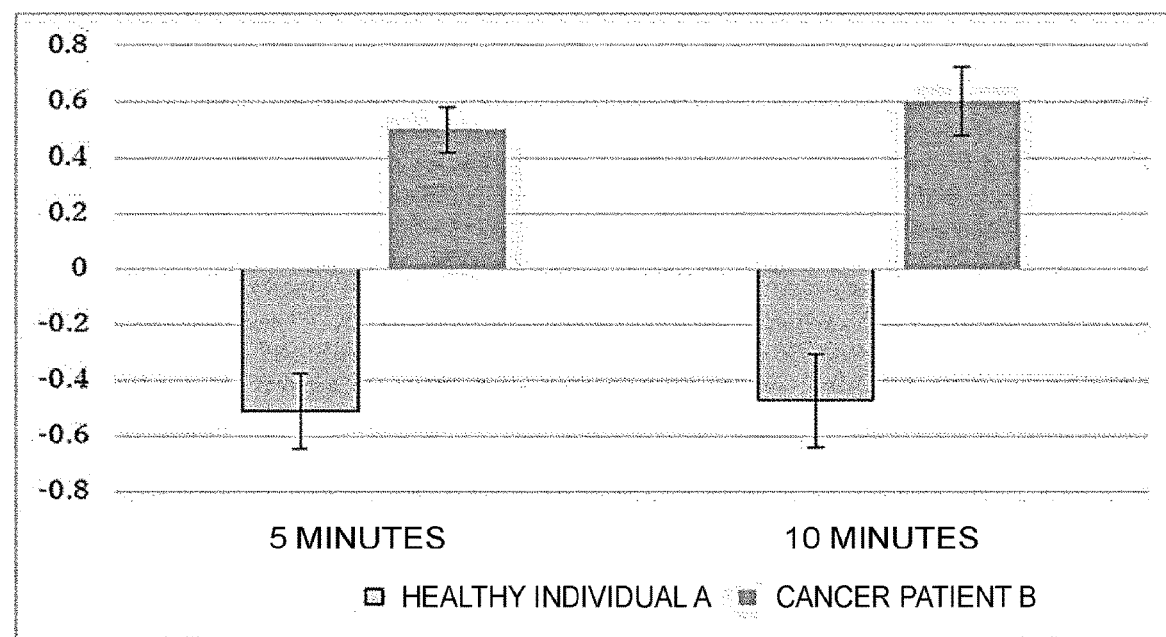
FIG. 6 is a graph showing that attraction behavior toward urine of a cancer patient and avoidance behavior from urine of a healthy individual can be clearly evaluated in 5 minutes and 10 minutes using the dish of the present invention.

As shown in FIG. 6, despite the high dilution factor, attraction behavior toward urine of the cancer patient and avoidance behavior from urine of the healthy individual could be clearly observed even after 5 minutes. The same results were obtained even after 10 minutes. Further, the taxic behavior indices in response to the urine sample of the cancer patient were 0.5 after 5 minutes and 0.6 after 10 minutes, which were good numerical values respectively indicating that 75% and 80% of nematodes showed attraction behavior.

Figure 7:
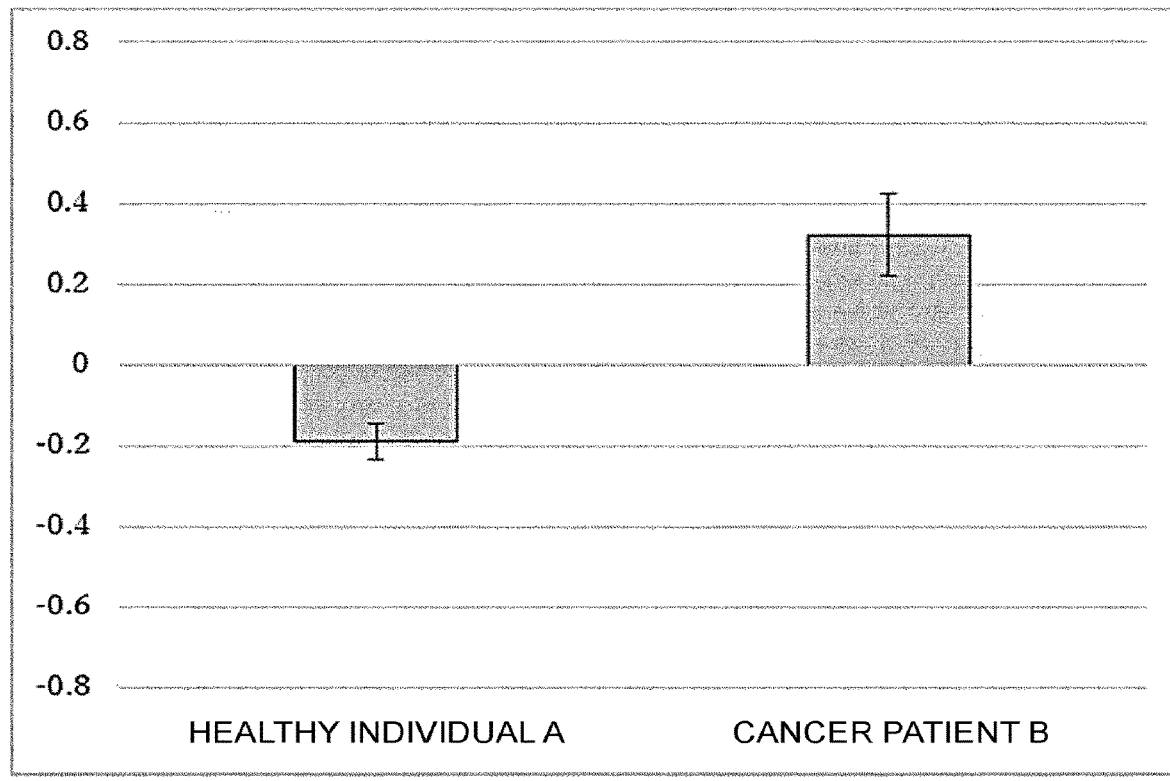
FIG. 7 is a graph showing the results of evaluating the taxic behavior in response to a urine sample based on a conventional method.

In contrast, the same experiment as in Example 1 of WO 2015/088039 was performed using a 9 cm dish under conditions of use of urine diluted 1/10, an assay time of 30 minutes, and use of sodium azide, as a result of which the taxis index was as low as only 0.3 (see FIG. 7). That is, only a low taxis index was observed in the system using the 9 cm dish despite the fact that the urine concentration was doubled.

Thereafter, the taxic behavior of nematodes was observed in the same conditions as in the experiment in which the results of FIG. 6 above were obtained, except that the concentration of urine was changed to 1/200 dilution, and the assay time was changed to 10 minutes in the evaluation method of this example. Urine obtained from a plurality of different cancer patients was used. The results were as shown in FIG. 8.

Figure 8:
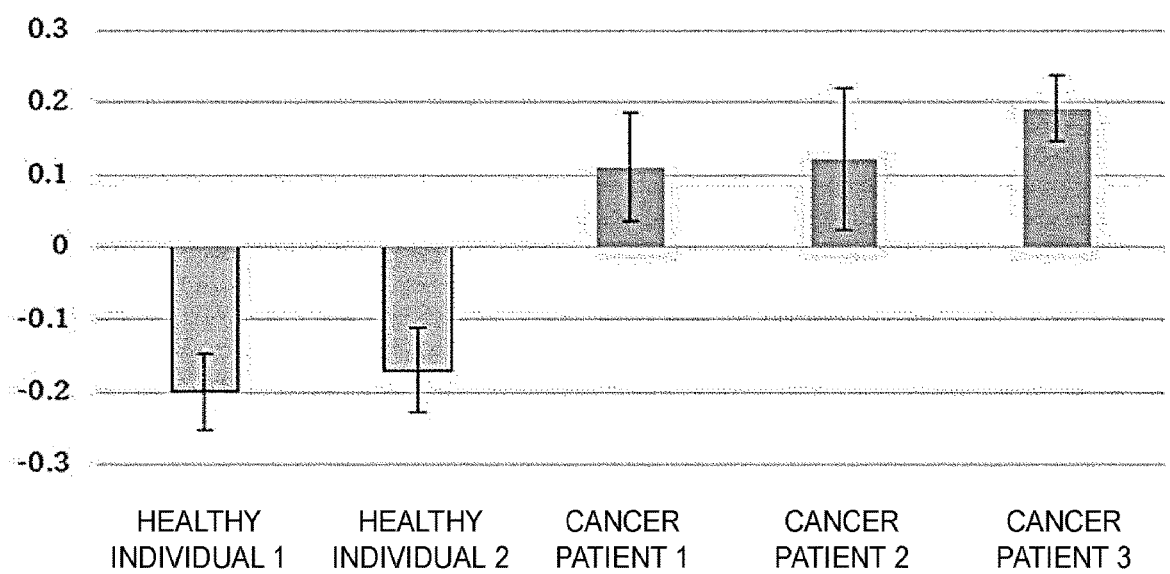
FIG. 8 is a graph showing the results of evaluating the taxic behavior using urine (1/200 dilution) obtained from various cancer patients and various healthy individuals.

As shown in FIG. 8, nematodes showed attraction behavior in response to urine from any cancer patient and avoidance behavior in response to urine of any healthy individuals. The taxis index was 0.1 to 0.2, despite the fact that urine was highly diluted, so that the high sensitivity of this evaluation method could be demonstrated. Meanwhile, the taxis index in response to urine of the healthy individual was also −0.15 to −0.2, so that the high sensitivity of this evaluation method could be revalidated.

Example 3: Evaluation of Taxic Behavior of Nematodes Using 3 cm×1 cm Rectangular Dish In this example, the taxic behavior of nematodes was evaluated using a rectangular dish that was further smaller than in Example 1.

The taxic behavior of nematodes was observed in the same conditions as in the experiment in which the results of FIG. 6 above were obtained, except that a 3 cm×1 cm rectangular dish was used. The evaluation was performed at 5 minutes and 10 minutes after the dissemination of nematodes. The results were as shown in FIG. 9.

Figure 9:
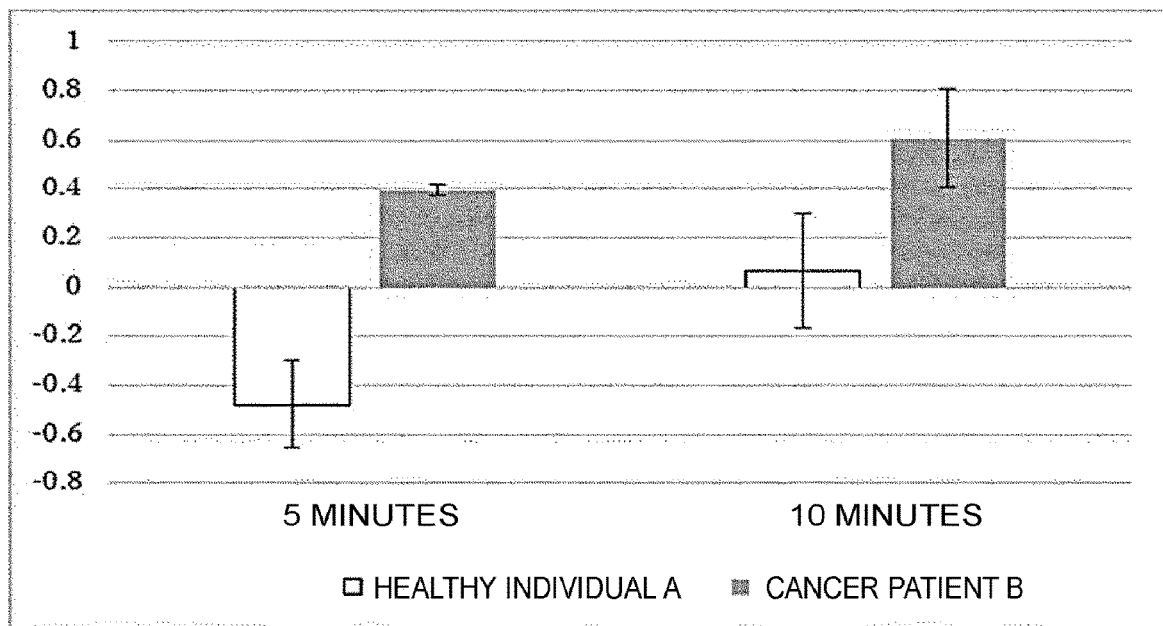
FIG. 9 is a graph showing the results of evaluating the taxic behavior using a 3 cm×1 cm rectangular dish.

As shown in FIG. 9, the nematodes showed attraction behavior in response to urine of the cancer patient and showed avoidance behavior in response to urine of the healthy individual, after a lapse of 5 minutes. Meanwhile, the nematodes showed attraction behavior in response to urine of the cancer patient but did not show avoidance behavior in response to urine of the healthy individual, after a lapse of 10 minutes.

These results indicated that the taxic behavior of nematodes can be evaluated even with a small rectangular dish but also suggested a possibility of a decrease in sensitivity, on the other hand.

As the causes for the decrease in sensitivity were investigated, one of the causes was revealed to be that the nematodes went over the sidewall of the dish, or the nematodes get under the culture medium along the sidewall, after a lapse of 10 minutes, as a result of which the number of countable nematodes decreased. That is, it was demonstrated that the position where the nematodes were arranged was preferably 0.5 cm or more away from the sidewall of the dish.

Example B4: Taxic Behavior Evaluation System According to Third Embodiment

In this example, a field (the recess 600) for evaluating the taxic behavior was provided in the solid medium, not in the dish itself, and the taxic behavior of nematodes was evaluated therein.

The taxic behavior based on olfactory sense was evaluated using N2 Bristol strains that are nematode strains. The nematodes were bred using a NGM plate shown in Table 1 below.

TABLE 1

Medium composition of NGM plate

| | |
|---|---|
| NaCl | 3 g/L |
| Bacto peptone | 2.5 g/L |
| Agar | 17 g/L |
| Cholesterol (5 mg/ml, in ethanol) | 1 ml/L |
| $KPO_4$ (pH 6.0) | 25 ml/L |
| $CaCl_2$ | 1 ml/L |
| $MgSO_4$ | 1 ml/L |

Further, the taxic behavior of nematodes was evaluated using an assay plate (a dish with a diameter of 5 cm or 9 cm) shown in Table 2 below.

TABLE 2

Medium composition of assay plate (5 cm or 9 cm diameter dish)

| | |
|---|---|
| Bacto agar | 20 g/L |
| $KPO_4$ (1M) | 5 ml/L |
| $CaCl_2$ (1M) | 1 ml/L |
| $MgSO_4$ (1M) | 1 ml/L |

After a reagent was mixed using the culture medium composition of the assay plate, followed by autoclaving, an appropriate amount of the reagent was poured into a 9 cm dish, and the solid medium was solidified by cooling while pressing a plastic plate of 5 cm×2 cm×1 mm against the surface. After the solid medium was solidified, the plastic plate was removed, to form a recess with a length of 5 cm, a width of 2 cm, and a depth of 1 mm on the surface of the solid medium. Thus, a dish including a solid medium having a surface with a recess as shown in FIGS. 11A and B was obtained.

Figure 13:
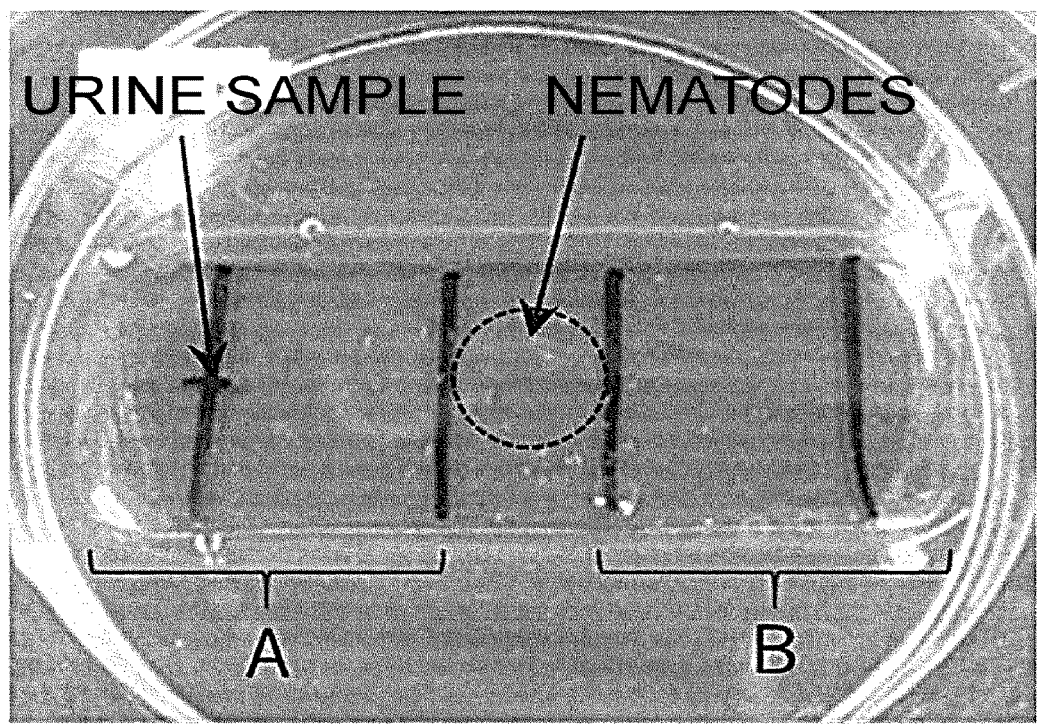
FIG. 13 is an image of the evaluation system of the third embodiment of the present invention constructed in Example B4.

Then, isoamyl alcohol (IAA) diluted $10^{-5}$-fold or nonanone (Nona) diluted $10^{-3}$-fold was arranged at the position shown by the symbol "+" on the right side of FIG. 13, and nematodes cultured at 20° C. for 4 days were arranged at the center (which corresponded to region B in FIG. 13). Thereafter, the taxic behavior of nematodes at 23° C. was observed.

Further, comparison with the observation results using the behavior evaluation system used in Examples 1 and 2 was performed.

The number of nematodes in the regions corresponding to regions A, B, and C in FIG. 13 were counted after a lapse of 0 minutes, 5 minutes, 10 minutes, and 20 minutes. The number of nematodes remaining was calculated as a ratio of the number of nematodes in response to the number of nematodes at 0 minutes at each time. Further, the taxis index was calculated based on the formula [N (A)−N (B)]/[N (A)+N (B)]. Here, N (A) is the number of nematodes that moved to region A, and N (B) is the number of nematodes that moved to region B.

Figure 14:
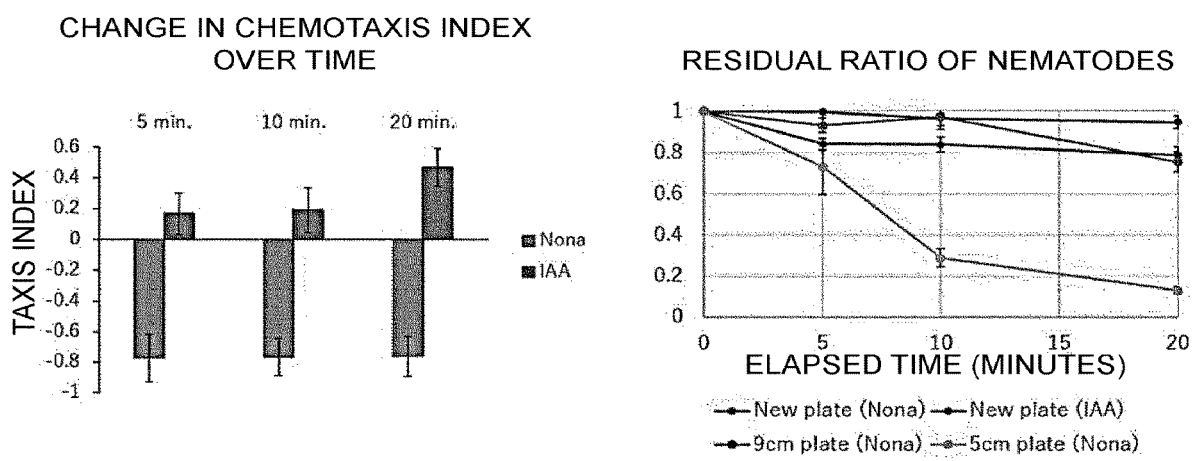
FIG. 14 shows the evaluation results for the taxic behavior of nematodes using the evaluation system of the third embodiment of the present invention constructed in Example B4 (left) and shows a time-dependent change (right) in the proportion of the nematodes remaining on the surface observed.

The results were as shown in FIG. 14. As shown in the right side of FIG. 14, nematodes penetrated into the gap between the solid medium and the plate sidewall with a lapse of time (horizontal axis, unit: minute), so that nematodes on the observation surface decreased, in the behavior evaluation system (5 cm plate (Nona)) used in Examples 1 and 2. In contrast, a reduction in nematodes on the observation surface with a lapse of time was hardly observed in the evaluation system of the third embodiment (New plate (Nona) and New plate (IAA)). Further, as shown in the left side of FIG. 14, avoidance behavior in response to nonanone (Nona) could be clearly observed at 5 minutes in the evaluation system of the third embodiment. Further, migration behavior to isoamyl alcohol (IAA) could be clearly observed at 5 minutes, particularly, 20 minutes in the evaluation system of the third embodiment. Referring to the right side of FIG. 14 together, a reduction in nematodes was suppressed also after 20 minutes when the results became clear by using the evaluation system of the third embodiment, and it is considered that there is a large merit for clarifying the observation results.

The invention claimed is:

1. A taxic behavior evaluation system for evaluating the taxic behavior of *Caenorhabditis elegans* (*C. elegans*), comprising:
    a bottom surface having a shape of 3 cm to 6 cm in the longitudinal direction and 1 cm to 3 cm in the transverse direction; and
    a sidewall surrounding the periphery of the bottom surface, wherein
    the bottom surface is partitioned by marks into at least three regions of a first region, a second region, and a third region from an end on one side toward the other end in the longitudinal direction, and
    the second region is arranged at the boundary between the first region and the third region.

2. The taxis behavior evaluation system according to claim 1, wherein
    the marks are made by forming an indented shape or printing on the upper surface or an indented shape or printing on the lower surface of the bottom surface.

3. The taxic behavior evaluation system according to claim 1, further comprising:
    an indicator to distinguish the first region and the third region from each other.

4. A multiplate comprising:
    a plurality of taxic behavior evaluation systems according to claim 1 that are connected together.

5. A taxic behavior evaluation system for evaluating the taxic behavior of *Caenorhabditis elegans* (*C. elegans*), comprising:
    a dish in which a solid medium having a surface with a substantially rectangular planar recess is introduced, wherein the depth of the recess is equal to or larger than the thickness of the *C. elegans* and the depth is 2 mm or less; and
    a plate that covers the recess from above.

6. The taxic behavior evaluation system according to claim 5, wherein
    a site corresponding to the recess, on the bottom surface of the dish is partitioned by marks into at least three regions of a first region, a second region, and a third region from an end on one side toward the other end in the longitudinal direction, and the second region is arranged at the boundary between the first region and the third region.

7. The taxic behavior evaluation system according to claim 5, wherein a site, corresponding to the recess, of the plate that covers the recess from above is partitioned by marks into at least three regions of a first region, a second region, and a third region from an end on one side toward the other end in the longitudinal direction, and the second region is arranged at the boundary between the first region and the third region.

8. The taxic behavior evaluation system according to claim 6, wherein the marks are made by forming an indented shape or printing on the upper surface or the lower surface of the bottom surface.

9. The system for evaluating the taxic behavior of *C. elegans* according to claim 1, wherein the first region and the third region are in contact with each other, and the second region is closed.

10. The taxic behavior evaluation system according to claim 1, further comprising:

a lid comprising a test sample seat on a surface opposed to the bottom surface when the lid is closed.

11. The taxic behavior evaluation system according to claim 1, wherein the *C. elegans* are arranged in the second region.

12. The taxic behavior evaluation system according to claim 1, wherein a test sample is arranged in the first region or the third region.

* * * * *